(12) United States Patent
Kobayashi et al.

(10) Patent No.: US 12,029,746 B2
(45) Date of Patent: Jul. 9, 2024

(54) ORAL COMPOSITION

(71) Applicant: KAO CORPORATION, Tokyo (JP)

(72) Inventors: Yusuke Kobayashi, Meguro-ku (JP); Yuichi Shimoda, Ichikawa (JP); Hiroko Uchida, Koto-ku (JP); Sho Aida, Yokohama (JP); Shun Sakoda, Soka (JP)

(73) Assignee: KAO CORPORATION, Tokyo (JP)

( * ) Notice: Subject to any disclaimer, the term of this patent is extended or adjusted under 35 U.S.C. 154(b) by 724 days.

(21) Appl. No.: 17/254,674

(22) PCT Filed: Jun. 20, 2019

(86) PCT No.: PCT/JP2019/024495
§ 371 (c)(1),
(2) Date: Dec. 21, 2020

(87) PCT Pub. No.: WO2019/244976
PCT Pub. Date: Dec. 26, 2019

(65) Prior Publication Data
US 2021/0220382 A1    Jul. 22, 2021

(30) Foreign Application Priority Data

Jun. 22, 2018 (JP) ................................. 2018-118569
Nov. 6, 2018 (JP) ................................. 2018-209228

(51) Int. Cl.
| | | |
|---|---|---|
| A61K 31/7048 | (2006.01) | |
| A23L 27/00 | (2016.01) | |
| A23L 27/10 | (2016.01) | |
| A23L 27/30 | (2016.01) | |
| A23L 33/00 | (2016.01) | |
| A61K 9/16 | (2006.01) | |
| A61K 9/20 | (2006.01) | |
| A61K 9/68 | (2006.01) | |
| A61K 31/11 | (2006.01) | |
| A61K 31/352 | (2006.01) | |

(52) U.S. Cl.
CPC .......... *A61K 31/7048* (2013.01); *A23L 27/10* (2016.08); *A23L 27/33* (2016.08); *A23L 27/88* (2016.08); *A23L 33/30* (2016.08); *A61K 9/0058* (2013.01); *A61K 9/16* (2013.01); *A61K 9/20* (2013.01); *A61K 31/11* (2013.01); *A61K 31/352* (2013.01)

(58) Field of Classification Search
CPC ..... A61K 31/7048; A61K 31/11; A23L 27/10; A23L 27/33; A23L 27/88; A23L 33/30; A23G 9/32
See application file for complete search history.

(56) References Cited

U.S. PATENT DOCUMENTS

| | | |
|---|---|---|
| 7,211,567 B1 | 5/2007 | Kotani et al. |
| 2008/0113044 A1 | 5/2008 | Alberte et al. |
| 2017/0000150 A1 | 1/2017 | Cilliers et al. |

FOREIGN PATENT DOCUMENTS

| | | |
|---|---|---|
| CA | 2 584 092 A1 | 10/2007 |
| JP | 2002-291441 A | 10/2002 |
| JP | 3090715 U | 12/2002 |
| JP | 2003-95968 A | 4/2003 |
| JP | 2005-278478 A | 10/2005 |
| JP | 2006-129757 A | 5/2006 |
| JP | 2008-295370 A | 12/2008 |
| JP | 2012-21009 A | 2/2012 |
| JP | 2017-504317 A | 2/2017 |
| JP | WO 2017/030187 A1 | 2/2017 |
| JP | 2017-93410 A | 6/2017 |
| JP | 2017-112935 A | 6/2017 |
| JP | WO 2018-150571 A | 8/2018 |
| JP | 2018-157792 A | 10/2018 |
| JP | 2019-41738 A | 3/2019 |
| JP | WO 2019/049264 A1 | 3/2019 |
| JP | 2019-62845 A | 4/2019 |

OTHER PUBLICATIONS

Yashin et al., Journal of Food Research, 2015, 4(3), p. 56-87. (Year: 2015).*
Martini et al., Food Research International, 2018, 112, p. 1-16, Available online Jun. 8, 2018. (Year: 2018).*
Gaudette et al., Chem. Percept., 2016, 9, p. 1-7. (Year: 2016).*
"Delicious mulberry leaf green juice," Ohta's Isan Health Food Museum, Retrieved from the Internet on Jul. 1, 2021, 2015, 32 pages (with English machine translation).
"Ohta's Isan 60 bags of delicious mulberry leaf green juice," Amazon.co.jp, Retrieved from the Internet on Jun. 16, 2021 [URL: https://www.amazon.co.jp/gp/product/B01K1IAPC8/ref=ppx_yo_dt_b_asin_title_o02_s01?ie=UTF8&psc=1], Aug. 8, 2016, 13 pages (with English machine translation).
"Calorie Limit Tea," FANCL Online, Retrieved from the Internet on Jul. 1, 2021 [URL: https://www.fancl.co.jp/healthy/item/5294a/], Dec. 15, 2015, 4 pages (with English machine translation).
"Review of Calorie Limit Tea," FANCL Online, Retrieved from the Internet on Jun. 16, 2021, [URL: https://www.fancl.co.jp/healthy/reviews/5294a], Dec. 15, 2015, 36 pages (with English machine translation).

(Continued)

*Primary Examiner* — Jonathan S Lau
(74) *Attorney, Agent, or Firm* — Oblon, McClelland, Maier & Neustadt, L.L.P.

(57) ABSTRACT

Provided is an oral composition, including the following components (A), (B), and (C): (A) non-polymer catechins; (B) rutin; and (C) astragalin, wherein a content of the component (A) in solids is from 2 mass % to 50 mass %, wherein a mass ratio between the component (A) and the component (B), [(B)/(A)], is from $0.05 \times 10^{-2}$ to $50 \times 10^{-2}$, and wherein a mass ratio between the component (A) and the component (C), [(C)/(A)], is from $1.0 \times 10^{-3}$ to $50 \times 10^{-3}$.

15 Claims, No Drawings

(56) References Cited

OTHER PUBLICATIONS

Analysis test report of "delicious mulberry leaf green juice" (Astragalin, Rutin and Catechins), and flowchart of analysis method on Astragalin, Rutin and Catechins, Japan Food Research Laboratories Center, Feb. 23, 2021, 9 pages (with English machine translation).

Analysis test report of "delicious mulberry leaf green juice" (Vanillin), and flowchart of analysis method on Vanillin, Japan Food Research Laboratories Center, May 13, 2021, 4 pages (with English machine translation).

"Calorie Limit Tea" Analytical Test Report (Astragalin, Rutin and Catechins), and flowchart of analysis method on Astragalin, Rutin and Catechins, Japan Food Research Laboratories Center, Apr. 13, 2021, 10 pages (with English machine translation).

"Calorie Limit Tea" Analytical Test Report (Vanillin), and flowchart of analysis method on Vanillin, Japan Food Research Laboratories Center, May 13, 2021, 4 pages (with English machine translation).

Photograph of "delicious mulberry leaf green juice," Ohta's Isan Co., Ltd., 2015, 3 pages (with English machine translation).

Ohkura, T. et al., "A Study on Daily Intake of Polyphenols and Furanocoumarins in Health-promoting Food Based on Simultaneous Determination of Amount of These Compounds," (With unedited computer-generated English translation) Ehime Kanken Annual Report, 2010, No. 13, total pp. 21).

Cocconi, E. et al., "Characterization of polyphenols in apricot and peach purees by UHPLC coupled to HRMS Q-Exactive™ mass spectrometer: an approach in the identification of adulterations," Journal of Mass Spectrometry, 2016, vol. 51, pp. 742-749.

Qian, Z-M. et al., "Identification and Quantification of Free Radical Scavengers in Pu-erh Tea by HPLC-DAD-MS Coupled Online with 2,2'-Azinobis(3-ethylbenzthiazolinesulfonic acid) Diammonium Salt Assay," Journal of Agricultural and Food Chemistry, 2008, vol. 56, pp. 11187-11191.

Riaz, A. et al., "Astragalin: A Bioactive Phytochemical with Potential Therapeutic Activities," Advances in Pharmacological Sciences, May 2, 2018, pp. 1-15. (16 total pages).

Luo, Z-M. et al., "A New Norisoprenoid and Other Compounds from Fuzhuan Brick Tea," Molecules, 2012, vol. 17, pp. 3539-3546.

Wang, R. et al., "Comparative study on component analysis and in vitro functional effects of Xiaguan raw and ripe bowl tea," Science and Technology of Food Industry, 2014, vol. 35, No. 6, pp. 150-155. (with English abstract and partial English translation).

International Search Report issued on Jul. 30, 2019 in PCT/JP2019/024495 filed on Jun. 20, 2019, 4 pages.

Extended European Search Report issued Mar. 7, 2022 in corresponding European Patent Application No. 19823438.7, 8 pages.

Kosakowska, O. K., et al., "Intraspecific variability in the content of phenolic compounds, essential oil and mucilage of small-leaved lime (*Tilia cordata* Mill.) from Poland", Industrial Crops and Products, vol. 78, Oct. 27, 2015, pp. 58-65.

* cited by examiner

ORAL COMPOSITION

CROSS REFERENCE TO RELATED APPLICATION

This application is a national stage entry under 35 USC 371 of PCT/JP2019/024495, filed on Jun. 20, 2019, and claims priority to Japanese Patent Applications No. 2018-118569 filed on Jun. 22, 2018, and No. 2018-209228 filed on Nov. 6, 2018,

FIELD OF THE INVENTION

The present invention relates to an oral composition.

BACKGROUND OF THE INVENTION

Non-polymer catechins and rutin are a polyphenol compound, respectively, and have various physiological activities. An investigation has been made on a food composition exhibiting a high physiological effect by combining a plurality of polyphenols (Patent Document 1). Meanwhile, the non-polymer catechins have unpleasant tastes, such as bitterness and harshness, and the unpleasant tastes are known to be further enhanced in the presence of another flavonoid (Patent Document 2).

Meanwhile, astragalin is a polyphenol compound contained in persimmon leaves and mulberry leaves, and has been reported to have an antiallergic action. With attention focused on such physiological action, investigations have been made on application of astragalin to foods and beverages. For example, there is a report that absorbability of astragalin is improved by blending astragalin with one or more of sugars selected from the group consisting of fructose, galactose, lactose, and glucose (Patent Document 3).

[Patent Document 1] JP-A-2003-95968
[Patent Document 2] JP-A-2006-129757
[Patent Document 3] JP-A-2002-291441

SUMMARY OF THE INVENTION

The present invention provides an oral composition, comprising the following components (A), (B), and (C):
(A) non-polymer catechins;
(B) rutin; and
(C) astragalin,
wherein a content of the component (A) in solids is from 2 mass % to 50 mass %,
wherein a mass ratio between the component (A) and the component (B), [(B)/(A)], is from 0 05×10$^{-2}$ to 50× 10$^{-2}$, and
wherein a mass ratio between the component (A) and the component (C), [(C)/(A)], is from 1.0×10$^{-3}$ to 50×10$^{-3}$.

The present invention also provides a food and beverage having the above-mentioned oral composition added thereto.

DETAILED DESCRIPTION OF THE INVENTION

The inventors of the present invention found that the bitterness of non-polymer catechins in the presence of another flavonoid is even more enhanced when the non-polymer catechins are highly concentrated and eaten as a supplement or a seasoning.

The present invention relates to an oral composition that, even though being rich in non-polymer catechins and rutin, is reduced in bitterness of the non-polymer catechins.

The inventors of the present invention made extensive investigations in view of the above-mentioned problem. As a result of that, they surprisingly found that the bitterness of the non-polymer catechins is markedly reduced by causing an oral composition comprising the non-polymer catechins and rutin at a specific quantitative ratio to comprise astragalin, which is known to be essentially a bitterness substance, at a predetermined quantitative ratio with respect to the non-polymer catechins.

According to the present invention, it can provide an oral composition that, even though being rich in non-polymer catechins and rutin, is reduced in bitterness of the non-polymer catechins.

<Oral Composition>

As used herein, the term "oral composition" refers to a product to be orally ingested. A product form of the oral composition may be a solid form or a liquid form at ordinary temperature (20° C.±15° C.), and is not particularly limited. In the case of the liquid form, any of the following forms may be adopted: a concentrated liquid form, a gel form, a jelly form, and a slurry form. In the case of the concentrated liquid form, a solid concentration thereof may be appropriately selected as long as the concentration is higher than that of a ready-to-drink (RTD), and is not particularly limited. Examples of the solid form may include a powder form, a granule form, a tablet form, a rod form, a plate form, and a block form. When the oral composition is in the solid form, solids content in the oral composition is generally 80 mass % or more, preferably 90 mass % or more, more preferably 93 mass % or more, more preferably 95 mass % or more, even more preferably 97 mass % or more. The upper limit of such solids content is not particularly limited, and may be 100 mass %. As used herein, the term "solids content" refers to the mass of a residue obtained by drying a sample in an electric thermostat dryer at 105° C. for 3 hours to remove volatile substances. Of those, the product form of the oral composition is preferably a solid form, a concentrated liquid form, or a jelly form, more preferably a solid form or a concentrated liquid form, even more preferably a solid form. Of the solid forms, a tablet form or a granule form is preferred.

The oral composition of the present invention comprises non-polymer catechins as a component (A). As used herein, the term "(A) non-polymer catechins" is a generic term for non-gallate forms, such as catechin, gallocatechin, epicatechin, and epigallocatechin, and gallate forms, such as catechin gallate, gallocatechin gallate, epicatechin gallate, and epigallocatechin gallate. In the present invention, at least one of the eight species may be contained.

The origin of the component (A) is not particularly limited as long as the component (A) is a component generally used in the field of foods and beverages. For example, the component (A) may be a chemically synthesized product, or may be a plant extract containing non-polymer catechins, such as a tea extract. When the plant extract is used as the component (A), an extraction method and extraction conditions for the plant extract are not particularly limited, and a known method may be adopted.

A content of the component (A) in solids of the oral composition of the present invention is from 2 mass % to 50 mass %. The content of the component (A) is preferably 2.5 mass % or more, more preferably 3 mass % or more, more preferably 4 mass % or more, even more preferably 5 mass % or more, from the viewpoints of the enhancement of the non-polymer catechins, and physiological effects, and is preferably 40 mass % or less, more preferably 30 mass % or less, even more preferably 20 mass % or less, from the viewpoint of a reduction in bitterness derived from the component (A). The content of the component (A) in the solids of the oral composition of the present invention falls within the range of preferably from 2.5 mass % to 40 mass %, more preferably from 2.5 mass % to 30 mass %, more preferably from 3 mass % to 20 mass %, more preferably from 4 mass % to 20 mass %, even more preferably from 5 mass % to 20 mass %. The content of the component (A) is defined on the basis of the total amount of the eight non-polymer catechins. In addition, the content of the component (A) may be measured by an analysis method suitable for the state of a measurement sample among generally known measurement methods, and for example, may be analyzed by liquid chromatography. A specific example thereof is a method described in Examples to be described later. At the time of the measurement of the content, the necessary treatment as described below may be appropriately performed: the sample is freeze-dried for adapting it to the detection range of an apparatus; or contaminants in the sample are removed for adapting it to the resolution of the apparatus.

In the oral composition of the present invention, the kind of the component (A) is not particularly limited, but a ratio of gallate forms in the non-polymer catechins is preferably from 0 mass % to 75 mass %, more preferably from 20 mass % to 68 mass %, more preferably from 30 mass % to 65 mass %, more preferably from 35 mass % to 63 mass %, even more preferably from 40 mass % to 58 mass %, from the viewpoint of a reduction in bitterness. As used herein, the term "ratio of gallate forms" refers to the mass ratio of the above-mentioned four gallate forms to the eight non-polymer catechins.

The oral composition of the present invention comprises rutin as a component (B). As used herein, the term "rutin" refers to a compound in which β-rutinose is added to the hydroxy group at the 3-position of quercetin. The component (B) may be derived from a raw material, or may be newly added. In addition, the origin of the component (B) is not particularly limited as long as the component (B) is a component generally used in the field of foods and beverages. For example, the component (B) may be a chemically synthesized product, or may be a plant extract containing rutin. When the plant extract is used as the component (B), an extraction method and extraction conditions for the plant extract are not particularly limited, and a known method may be adopted.

A content of the component (B) in the oral composition of the present invention is preferably 0.005 mass % or more, more preferably 0.01 mass % or more, even more preferably 0.03 mass % or more, from the viewpoint of physiological effects, and is preferably 1.0 mass % or less, more preferably 0.6 mass % or less, more preferably 0.3 mass % or less, even more preferably 0.2 mass % or less, from the viewpoints of a reduction in bitterness derived from the component (A), and the suppression of an astringent taste derived from the component (B). The content of the component (B) in the solids of the oral composition of the present invention falls within the range of preferably from 0.005 mass % to 1.0 mass %, more preferably from 0.01 mass % to 0.6 mass %, more preferably from 0.03 mass % to 0.3 mass %, even more preferably from 0.03 mass % to 0.2 mass %. The content of the component (B) may be measured by an analysis method suitable for the state of a measurement sample among generally known measurement methods, and for example, may be analyzed by liquid chromatography. A specific example thereof is a method described in Examples to be described later. At the time of the measurement of the content, the necessary treatment as described below may be appropriately performed: the sample is freeze-dried for adapting it to the detection range of an apparatus; or contaminants in the sample are removed for adapting it to the resolution of the apparatus.

The oral composition of the present invention comprises astragalin as a component (C). As used herein, the term "astragalin" refers to a compound in which glucose is added to the hydroxy group at the 3-position of kaempferol. The component (C) may be derived from a raw material, or may be newly added. In addition, the origin of the component (C) is not particularly limited as long as the component (C) is a component generally used in the field of foods and beverages. For example, the component (C) may be a chemically synthesized product, or may be a plant extract containing astragalin. When the plant extract is used as the component (C), an extraction method and extraction conditions for the plant extract are not particularly limited, and a known method may be adopted.

From the viewpoint of a reduction in bitterness derived from the component (A), a content of the component (C) in the oral composition of the present invention is preferably 0.005 mass % or more, more preferably 0.01 mass % or more, more preferably 0.02 mass % or more, more preferably 0.04 mass % or more, more preferably 0.06 mass % or more, even more preferably 0.08 mass % or more, and is preferably 1.0 mass % or less, more preferably 0.8 mass % or less, more preferably 0.5 mass % or less, even more preferably 0.3 mass % or less. The content of the component (C) in the solids of the oral composition of the present invention falls within the range of preferably from 0.005 mass % to 1.0 mass %, more preferably from 0.01 mass % to 0.8 mass %, more preferably from 0.02 mass % to 0.5 mass %, more preferably from 0.04 mass % to 0.3 mass %, more preferably from 0.06 mass % to 0.3 mass %, even more preferably from 0.08 mass % to 0.3 mass %. The content of the component (C) may be measured by an analysis method suitable for the state of a measurement sample among generally known measurement methods, and for example, may be analyzed by liquid chromatography. A specific example thereof is a method described in Examples to be described later. At the time of the measurement of the content, the necessary treatment as described below may be appropriately performed: the sample is freeze-dried for adapting it to the detection range of an apparatus; or contaminants in the sample are removed for adapting it to the resolution of the apparatus.

In the oral composition of the present invention, a mass ratio between the component (A) and the component (B), [(B)/(A)], is from $0.05 \times 10^{-2}$ to $50 \times 10^{-2}$. The mass ratio [(B)/(A)] is preferably $0.06 \times 10^{-2}$ or more, more preferably $0.08 \times 10^{-2}$ or more, more preferably $0.1 \times 10^{-2}$ or more, more preferably $0.2 \times 10^{-2}$ or more, more preferably $0.5 \times 10^{-2}$ or more, more preferably $1.0 \times 10^{-2}$ or more, even more preferably $1.5 \times 10^{-2}$ or more, from the viewpoint of a reduction in bitterness derived from the component (A), and is preferably $40 \times 10^{-2}$ or less, more preferably $30 \times 10^{-2}$ or less, more preferably $20 \times 10^{-2}$ or less, more preferably $8.0 \times 10^{-2}$ or less, even more preferably $3.0 \times 10^{-2}$ or less, from the viewpoints of a reduction in bitterness derived from the component (A), and the suppression of the astringent taste derived from the component (B). Such mass ratio [(B)/(A)] falls within the range of preferably from $0.06 \times 10^{-2}$ to $40 \times 10^{-2}$, more preferably from $0.08 \times 10^{-2}$ to $30 \times 10^{-2}$, more preferably from $0.1 \times 10^{-2}$ to $20 \times 10^{-2}$, more preferably from $0.2 \times 10^{-2}$ to $8.0 \times 10^{-2}$, more preferably from $0.5 \times 10^{-2}$ to $8.0 \times 10^{-2}$, more preferably from $1.0 \times 10^{-2}$ to $8.0 \times 10^{-2}$, even more preferably from $1.5 \times 10^{-2}$ to $3.0 \times 10^{-2}$.

In the oral composition of the present invention, a mass ratio between the component (A) and the component (C), [(C)/(A)], is from $1.0 \times 10^{-3}$ to $50 \times 10^{-3}$. From the viewpoint of a reduction in bitterness derived from the component (A), the mass ratio [(C)/(A)] is preferably $2.0 \times 10^{-3}$ or more, more preferably $3.0 \times 10^{-3}$ or more, more preferably $4.0 \times 10^{-3}$ or more, more preferably $5.0 \times 10^{-3}$ or more, even more preferably $7.0 \times 10^{-3}$ or more, and is preferably $40 \times 10^{-3}$ or less, more preferably $30 \times 10^{-3}$ or less, more preferably $20 \times 10^{-3}$ or less, even more preferably $15 \times 10^{-3}$ or less. Such mass ratio [(C)/(A)] falls within the range of preferably from $2.0 \times 10^{-3}$ to $40 \times 10^{-3}$, more preferably from $3.0 \times 10^{-3}$ to $30 \times 10^{-3}$, more preferably from $4.0 \times 10^{-3}$ to $30 \times 10^{-3}$, more preferably from $5.0 \times 10^{-3}$ to $20 \times 10^{-3}$, even more preferably from $7.0 \times 10^{-3}$ to $15 \times 10^{-3}$.

The oral composition of the present invention may comprise vanillin as a component (D). As used herein, the term "vanillin" refers to a main component of an aroma of vanilla, and vanillin is generally used as a flavor in the field of foods and beverages. The component (D) may be derived from a raw material, or may be newly added. In addition, the origin of the component (D) is not particularly limited as long as the component (D) is a component generally used in the field of foods and beverages. For example, the component (D) may be a chemically synthesized product, or may be a plant extract containing vanillin. When the plant extract is used as the component (D), an extraction method and extraction conditions for the plant extract are not particularly limited, and a known method may be adopted.

In the oral composition of the present invention, a content of the component (D) in the solids is preferably $0.05 \times 10^{-4}$ mass % or more, more preferably $0\ 0.1 \times 10^{-4}$ mass % or more, more preferably $0.2 \times 10^{-4}$ mass % or more, even more preferably $0.5 \times 10^{-4}$ mass % or more, from the viewpoints of a reduction in bitterness derived from the component (A), and the impartment of an aroma of green tea, and is preferably $100 \times 10^{-4}$ mass % or less, more preferably $60 \times 10^{-4}$ mass % or less, more preferably $40 \times 10^{-4}$ mass % or less, more preferably $20 \times 10^{-4}$ mass % or less, even more preferably $8.0 \times 10^{-4}$ mass % or less, from the viewpoint of the suppression of a sweet aroma derived from the component (D). Such content of the component (D) in the solids of the oral composition of the present invention falls within the range of preferably from $0.05 \times 10^{-4}$ mass % to $100 \times 10^{-4}$ mass %, more preferably from $0.1 \times 10^{-4}$ mass % to $60 \times 10^{-4}$ mass %, more preferably from $0.2 \times 10^{-4}$ mass % to $40 \times 10^{-4}$ mass %, more preferably from $0.5 \times 10^{-4}$ mass % to $20 \times 10^{-4}$ mass %, even more preferably from $0.5 \times 10^{-4}$ mass % to $8.0 \times 10^{-4}$ mass %. The content of the component (D) may be measured by an analysis method, such as a GC/MS method, suitable for the state of a measurement sample among generally known analysis methods. A specific example thereof is a method described in Examples to be described later. At the time of the measurement of the content, the necessary treatment as described below may be appropriately performed: the sample is freeze-dried for adapting it to the detection range of an apparatus; or contaminants in the sample are removed for adapting it to the resolution of the apparatus.

The oral composition of the present invention may comprise, as desired, one or more of additives, such as a sweetener, an acidulant, carbon dioxide gas, a flavor, a vitamin, a mineral, an antioxidant, an ester, an emulsifier, a preservative, a seasoning, a fruit juice extract, a vegetable extract, a nectar extract, and a quality stabilizer. A content of the additive may be appropriately set within a range that does not impair the purpose of the present invention.

In addition, the oral composition of the present invention may comprise an acceptable carrier as required. Examples of the carrier include: excipients (e.g., starch or starch degradation products, such as dextrin, monosaccharides, such as glucose, galactose, and fructose, disaccharides, such as sucrose, lactose, and palatinose, and sugar alcohols, such as maltitol, xylitol, sorbitol, and reduced palatinose); binders (e.g., hydroxypropyl methylcellulose, hydroxypropyl cellulose, gelatin, pregelatinized starch, polyvinylpyrrolidone, polyvinyl alcohol, pullulan, methyl cellulose, and hydrogenated oil); disintegrants (e.g., carmellose, carmellose calcium, croscarmellose sodium, crospovidone, corn starch, and low-substituted hydroxypropyl cellulose); lubricants (e.g., calcium stearate, magnesium stearate, sucrose fatty acid esters, sodium stearyl fumarate, talc, and silicon dioxide); taste-masking agents (e.g., *stevia*); and oligosaccharides, agar, crystalline cellulose, light anhydrous silicic acid, calcium hydrogen phosphate, extenders, surfactants, dispersants, buffers, and diluents. A content of the carrier may be appropriately set within a range that does not impair the purpose of the present invention.

Specific examples of the oral composition of the present invention include foods and beverages including: an instant beverage; a concentrated beverage; dairy products, such as a dairy beverage, yogurt, and cheese; and confectionery, such as jelly, chocolate, a candy, a snack, a biscuit, and rice confectionery. The oral composition may also be a health food (e.g., a food with nutrient function claims, a food for specified health use, a dietary supplement, a health supplement, or any other supplement), a pharmaceutical, or a quasi-drug. The instant beverage or the concentrated beverage refers to a product to be diluted with or dissolved in a liquid and drunk as a beverage, and the liquid is not particularly limited as long as the liquid enables reconstitution into a beverage. Examples of the liquid include water, carbonated water, cow's milk, and soy milk, and the temperature of the liquid is not limited. In addition, as a dosage form in the case of a health food, a pharmaceutical, or a quasi-drug, there are given, for example, a granule, a tablet, a capsule, a powder, a pill, a chewable agent, and a troche. Of those, the oral composition is preferably an oral composition in a solid form or an oral composition in a concentrated liquid form, more preferably an instant beverage, a concentrated beverage, a jelly food, a granule, or a tablet, even more preferably an instant beverage or a granule.

In addition, when the oral composition is an instant beverage, the instant beverage may be, for example, any of the following: a product that is filled in a container, such as a bottle, and weighed in an amount of a cup with a spoon or the like before drinking; a cup type comprising an amount corresponding to a cup; and a stick type in which small portions each corresponding to a cup are individually packaged. In addition, when the oral composition is a concentrated beverage, an example thereof is such a portion-type dilution beverage that small portions each corresponding to a cup are individually packaged. The volume of the cup is preferably from 30 mL to 320 mL, and the volume of the content in the small-portion package may be appropriately set so as to be suitable for the volume of the cup. Of those, a type in which small portions each corresponding to a cup are individually packaged is preferred from the viewpoint that the effect of the present invention is sufficiently imparted thereto, and examples thereof may include a product to be subjected to stick pack and a product to be subjected to pillow package. In the small-portion packaging, packaging may be performed with a packaging material made of an aluminum metallized film or the like. The inside of the container and the inside of the packaging material may be filled with nitrogen gas, and the packaging material preferably has low oxygen permeability from the viewpoint of quality maintenance.

The oral composition of the present invention may be produced in accordance with a conventional method, and an appropriate method may be adopted. For example, the oral composition of the present invention may be produced by mixing the component (A), the component (B), and the component (C), and as required, the carrier and/or the additive, so that the content of the component (A), and the mass ratio between the component (A) and the component (B) and the mass ratio between the component (A) and the component (C) fall within the above-mentioned ranges. The mixing order of the component (A), the component (B), and the component (C) is not particularly limited. The components may be added in any order, or the three components may be simultaneously added. An appropriate method, such as stirring or shaking, may be adopted as a method for the mixing, and a mixing apparatus may be used. The mixing system of the mixing apparatus may be of a rotating vessel type or a fixed vessel type. As the rotating vessel type, for example, a horizontal cylinder type, a V-type, a double-cone type, or a cubic type may be adopted. In addition, as the fixed vessel type, for example, a ribbon type, a screw type, a conical screw type, a paddle type, a fluidized bed type, or a Phillips blender may be adopted. In addition, the oral composition may be produced as a granulated product by a known granulation method. Examples of the granulation method include spray granulation, fluidized bed granulation, compression granulation, tumbling granulation, stirring granulation, extrusion granulation, and powder coating granulation. Granulation conditions may be appropriately selected depending on the granulation method. In addition, when the oral composition is produced as a tablet, any of wet tabletting and dry tabletting may be adopted, and a known compression molding machine may be used. Further, in the case of a concentrated liquid form, there may be adopted a known concentration method, such as a normal-pressure concentration method involving vaporizing a solvent at normal pressure, a reduced-pressure concentration method involving vaporizing a solvent at reduced pressure, or a membrane concentration method involving removing a solvent by membrane separation.

<Food and Beverage>

A food and beverage of the present invention has the above-mentioned oral composition added thereto.

The food and beverage to which the oral composition is added is not particularly limited, but examples thereof may include: beverages, such as a carbonated beverage, a fruit juice beverage, a vegetable juice, a sports drink, an energy drink, a coffee beverage, a cocoa beverage, a tea beverage, a dairy beverage, a lactic acid bacteria beverage, and a soy milk beverage; desserts, such as yogurt, jelly, pudding, mousse, and mizu-yokan; chilled sweets or frozen sweets, such as ice cream, lactic ice, ice milk, and sherbet; confectionery, such as a cake, chocolate, a cookie, a biscuit, a pie, a cracker, a snack, chewing gum, a hard candy, a soft candy, nougat, jelly beans, a gummy candy, a sweet bun, a rice cracker, a chopped rice cake, a roasted mochi piece, and yokan; seasonings, such as tare sauce, tomato ketchup, sauce, noodle soup, and syrup; and cream, jam, bread, a fish jelly product, a processed meat product, a retort-packaged food, a canned food, a pickle, tsukudani, a dry rice seasoning, and a frozen food.

A method of adding the oral composition is not particularly limited, and examples thereof include: direct addition of the oral composition to the food and beverage; addition of the oral composition to the food and beverage after dilution of the oral composition with a liquid, such as water; coating or filling of a product with the oral composition; and use of the oral composition by being kneaded into a dough during a production process. It is only required that the food and beverage to be finally eaten comprise the oral composition. A suitable example of the addition method is a mode in which the oral composition is directly sprinkled on the food and beverage to be eaten.

An addition amount of the oral composition may be appropriately selected depending on the kind of the food and beverage, but the oral composition is added in an amount of generally from 0.01 part by mass to 30 parts by mass, preferably from 0.03 part by mass to 20 parts by mass, more preferably from 0.05 part by mass to 15 parts by mass, even more preferably from 0.1 part by mass to 10 parts by mass in terms of solids with respect to 100 parts by mass of the food and beverage.

The present invention further discloses the following oral compositions regarding the embodiments described above.

<1> An oral composition, comprising the following components (A), (B), and (C):
(A) non-polymer catechins;
(B) rutin; and
(C) astragalin,
wherein a content of the component (A) in solids is from 2.5 mass % to 40 mass %,
wherein a mass ratio between the component (A) and the component (B), [(B)/(A)], is from $0.05 \times 10^{-2}$ to $50 \times 10^{-2}$, and wherein a mass ratio between the component (A) and the component (C), [(C)/(A)], is from $3.0 \times 10^{-3}$ to $40 \times 10^{-3}$.

<2> An oral composition, comprising the following components (A), (B), and (C):
(A) non-polymer catechins;
(B) rutin; and
(C) astragalin,
wherein a content of the component (A) in solids is from 2.5 mass % to 40 mass %,
wherein a mass ratio between the component (A) and the component (B), [(B)/(A)], is from $0.05 \times 10^{-2}$ to $50 \times 10^{-2}$, and
wherein a mass ratio between the component (A) and the component (C), [(C)/(A)], is from $5.0 \times 10^{-3}$ to $40 \times 10^{-3}$.

<3> An oral composition, comprising the following components (A), (B), and (C):
(A) non-polymer catechins;
(B) rutin; and
(C) astragalin,
wherein a content of the component (A) in solids is from 3 mass % to 20 mass %,
wherein a mass ratio between the component (A) and the component (B), [(B)/(A)], is from $0.05 \times 10^{-2}$ to $50 \times 10^{-2}$, and
wherein a mass ratio between the component (A) and the component (C), [(C)/(A)], is from $5.0 \times 10^{-3}$ to $20 \times 10^{-3}$.

<4> An oral composition, comprising the following components (A), (B), and (C):
(A) non-polymer catechins;
(B) rutin; and
(C) astragalin,
wherein a content of the component (A) in solids is from 2.5 mass % to 40 mass %, wherein a mass ratio between the component (A) and the component (B), [(B)/(A)], is from $0.5\times10^{-2}$ to $8.0\times10^{-2}$, and wherein a mass ratio between the component (A) and the component (C), [(C)/(A)], is from $1.0\times10^{-3}$ to $50\times10^{-3}$.

<5> An oral composition, comprising the following components (A), (B), and (C):
(A) non-polymer catechins;
(B) rutin; and
(C) astragalin,
wherein a content of the component (A) in solids is from 3 mass % to 20 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $1.0\times10^{-3}$ to $50\times10^{-3}$.

<6> An oral composition, comprising the following components (A), (B), and (C):
(A) non-polymer catechins;
(B) rutin; and
(C) astragalin,
wherein a content of the component (A) in solids is from 2.5 mass % to 40 mass %,
wherein a mass ratio between the component (A) and the component (B), [(B)/(A)], is from $0.5\times10^{-2}$ to $8.0\times10^{-2}$, and
wherein a mass ratio between the component (A) and the component (C), [(C)/(A)], is from $3.0\times10^{-3}$ to $40\times10^{-3}$.

<7> An oral composition, comprising the following components (A), (B), and (C):
(A) non-polymer catechins;
(B) rutin; and
(C) astragalin,
wherein a content of the component (A) in solids is from 2.5 mass % to 40 mass %,
wherein a mass ratio between the component (A) and the component (B), [(B)/(A)], is from $0.5\times10^{-2}$ to $8.0\times10^{-2}$, and
wherein a mass ratio between the component (A) and the component (C), [(C)/(A)], is from $5.0\times10^{-3}$ to $40\times10^{-3}$.

<8> An oral composition, comprising the following components (A), (B), and (C):
(A) non-polymer catechins;
(B) rutin; and
(C) astragalin,
wherein a content of the component (A) in solids is from 3 mass % to 20 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $5.0\times10^{-3}$ to $20\times10^{-3}$.

<9> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 2.5 mass % to 40 mass %,
wherein a mass ratio between the component (A) and the component (B), [(B)/(A)], is from $0.5\times10^{-2}$ to $8.0\times10^{-2}$, and
wherein a mass ratio between the component (A) and the component (C), [(C)/(A)], is from $3.0\times10^{-3}$ to $40\times10^{-3}$.

<10> An oral composition, comprising the following components (A), (B), (C), and (D):
the following components (A), (B), and (C);
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 2.5 mass % to 40 mass %,
wherein a mass ratio between the component (A) and the component (B), [(B)/(A)], is from $0.5\times10^{-2}$ to $8.0\times10^{-2}$, and
wherein a mass ratio between the component (A) and the component (C), [(C)/(A)], is from $5.0\times10^{-3}$ to $40\times10^{-3}$.

<11> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 3 mass % to 20 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $5.0\times10^{-3}$ to $20\times10^{-3}$.

<12> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 3 mass % to 20 mass %,
wherein a mass ratio between the component (A) and the component (B), [(B)/(A)], is from $1.5\times10^{-2}$ to $8.0\times10^{-2}$, and
wherein a mass ratio between the component (A) and the component (C), [(C)/(A)], is from $5.0\times10^{-3}$ to $20\times10^{-3}$.

<13> An oral composition, comprising the following components (A), (B), (C), and (D):
(A) non-polymer catechins;
(B) rutin;
(C) astragalin; and
(D) from $0.5\times10^{-4}$ mass % to $8.0\times10^{-4}$ mass % of vanillin,
wherein a content of the component (A) in solids is from 3 mass % to 20 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $5.0\times10^{-3}$ to $20\times10^{-3}$.

<14> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 2.5 mass % to 40 mass %,
wherein the component (A) has a ratio of gallate forms of from 0 mass % to 75 mass %,
wherein a mass ratio between the component (A) and the component (B), [(B)/(A)], is from $0.5\times10^{-2}$ to $8.0\times10^{-2}$, and wherein a mass ratio between the component (A) and the component (C), [(C)/(A)], is from $3.0\times10^{-3}$ to $40\times10^{-3}$.

<15> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 3 mass % to 20 mass %,
wherein the component (A) has a ratio of gallate forms of from 0 mass % to 75 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $5.0\times10^{-3}$ to $20\times10^{-3}$.

<16> An oral composition, comprising the following components (A), (B), (C), and (D):
(A) non-polymer catechins;
(B) rutin;
(C) astragalin; and
(D) from $0.5\times10^{-4}$ mass % to $8.0\times10^{-4}$ mass % of vanillin,
wherein a content of the component (A) in solids is from 3 mass % to 20 mass %,
wherein the component (A) has a ratio of gallate forms of from 0 mass % to 75 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $5.0\times10^{-3}$ to $20\times10^{-3}$.

<17> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 2.5 mass % to 40 mass %,
wherein the component (A) has a ratio of gallate forms of from 35 mass % to 63 mass %,
wherein a mass ratio between the component (A) and the component (B), [(B)/(A)], is from $0.5\times10^{-2}$ to $8.0\times10^{-2}$, and
wherein a mass ratio between the component (A) and the component (C), [(C)/(A)], is from $3.0\times10^{-3}$ to $40\times10^{-3}$.

<18> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 2.5 mass % to 40 mass %,
wherein the component (A) has a ratio of gallate forms of from 35 mass % to 63 mass %,
wherein a mass ratio between the component (A) and the component (B), [(B)/(A)], is from $0.5\times10^{-2}$ to $8.0\times10^{-2}$, and
wherein a mass ratio between the component (A) and the component (C), [(C)/(A)], is from $5.0\times10^{-3}$ to $40\times10^{-3}$.

<19> An oral composition, comprising the following components (A), (B), (C), and (D):
(A) non-polymer catechins;
(B) rutin;
(C) astragalin; and
(D) from $0.2\times10^{-4}$ mass % to $40\times10^{-4}$ mass % of vanillin,
wherein a content of the component (A) in solids is from 3 mass % to 20 mass %,
wherein the component (A) has a ratio of gallate forms of from 35 mass % to 63 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $5.0\times10^{-3}$ to $20\times10^{-3}$.

<20> An oral composition, comprising the following components (A), (B), (C), and (D):
(A) non-polymer catechins;
(B) rutin;
(C) astragalin; and
(D) from $0.5\times10^{-4}$ mass % to $8.0\times10^{-4}$ mass % of vanillin,
wherein a content of the component (A) in solids is from 3 mass % to 20 mass %,
wherein the component (A) has a ratio of gallate forms of from 35 mass % to 63 mass %,
wherein a mass ratio between the component (A) and the component (B), [(B)/(A)], is from $1.0\times10^{-2}$ to $8.0\times10^{-2}$, and
wherein a mass ratio between the component (A) and the component (C), [(C)/(A)], is from $5.0\times10^{-3}$ to $20\times10^{-3}$.

<21> An oral composition, comprising the following components (A), (B), (C), and (D):
(A) non-polymer catechins;
(B) rutin;
(C) astragalin; and
(D) from $0.5\times10^{-4}$ mass % to $8.0\times10^{-4}$ mass % of vanillin,
wherein a content of the component (A) in solids is from 3 mass % to 20 mass %,
wherein the component (A) has a ratio of gallate forms of from 35 mass % to 63 mass %,
wherein a mass ratio between the component (A) and the component (B), [(B)/(A)], is from $1.5\times10^{-2}$ to $8.0\times10^{-2}$, and wherein a mass ratio between the component (A) and the component (C), [(C)/(A)], is from $5.0\times10^{-3}$ to $20\times10^{-3}$.

EXAMPLES

1. Analysis of Non-Polymer Catechins

A sample solution was filtered through a filter (0.45 μm), and was analyzed by a gradient method through use of a high-performance liquid chromatograph (model SCL-10AVP, manufactured by Shimadzu Corporation) equipped with an octadecyl group-introduced packed column for a liquid chromatograph (L-Column TM ODS 4.6 mmφ×250 mm, 5 μm: manufactured by Chemicals Evaluation and Research Institute, Japan) at a column temperature of 40° C. A product manufactured by Kurita Water Industries Ltd. was used as a standard product of non-polymer catechins, and the determination was conducted by a calibration curve method. The determination was performed by using a distilled water solution containing 0.1 mol/L of acetic acid as a solution A of a mobile phase and an acetonitrile solution containing 0.1 mol/L of acetic acid as a solution B thereof under the conditions of a sample injection volume of 10 μL and a UV detector wavelength of 280 nm. Gradient conditions are as described below.

Concentration Gradient Conditions

| Time (min) | Concentration (vol %) of solution A | Concentration (vol %) of solution B |
| --- | --- | --- |
| 0 | 97% | 3% |
| 5 | 97% | 3% |
| 37 | 80% | 20% |
| 43 | 80% | 20% |
| 43.5 | 0% | 100% |
| 48.5 | 0% | 100% |
| 49 | 97% | 3% |
| 60 | 97% | 3% |

2. Analysis of Rutin and Astragalin 2 g of a sample was taken, and 20 mL of methanol was added. The mixture was subjected to ultrasonic extraction for 5 minutes, and then the volume was adjusted to be fixed at 25 mL. Then, 1 mL of the resultant was taken, and the volume was adjusted to be fixed at 25 mL, followed by analysis by a gradient method through use of a high-performance liquid chromatograph (model LC-20 Prominence, manufactured by Shimadzu Corporation) equipped with a column (Cadenza CD-C18 3 µm, 4.6 mmφ×150 mm, Imtakt) at a column temperature of 40° C. The analysis was performed by using an acetonitrile solution containing 0.05 mass % of acetic acid as a solution C of a mobile phase and an acetonitrile solution as a solution D thereof under the conditions of a sample injection volume of 10 µL and a UV detector wavelength of 360 nm. Gradient conditions are as described below.

Concentration Gradient Conditions

| Time (min) | Concentration (vol %) of solution C | Concentration (vol %) of solution D |
| --- | --- | --- |
| 0 | 85% | 15% |
| 20 | 80% | 20% |
| 35 | 10% | 90% |
| 50 | 10% | 90% |
| 50.1 | 85% | 15% |
| 60 | 85% | 15% |

A solution having a known concentration was prepared using a standard product of rutin or astragalin, and subjected to high-performance liquid chromatographic analysis to measure a retention time and prepare a calibration curve, and rutin or astragalin in the sample solution was quantified.

3. Analysis of Vanillin 10 mL of a sample was taken in a headspace vial for GC (20 mL), and 4 g of sodium chloride was added thereto. A stirring bar was placed in the vial, and the vial was hermetically sealed. While the contents were stirred with a stirrer for 30 minutes, the contained components were allowed to adsorb onto SPME fiber (manufactured by Sigma-Aldrich, 50/30 µm, DVB/CAR/PDMS). After the adsorption, the SPME fiber was subjected to thermal desorption at the inlet, and GC/MS measurement was performed. Agilent 7890A/5975Cinert (manufactured by Agilent Technologies) was used as an analyzer.

Analysis conditions are as described below.
  Column: TC-WAX (30 m (length), 0.25 mm (inner diameter), 0.25 µm (film thickness))
  Column temperature: 40° C. (3 min)→20° C./min→250° C.
  Column pressure: constant flow rate mode (31 kPa)
  Column flow rate: 1 mL/min (He)
  Inlet temperature: 260° C.
  Injection mode: splitless
  Detector: MS
  Ion source temperature: 230° C.
  Ionization method: EI (70 eV)
  Scan range: SCAN A commercially-available reagent was dissolved in ethanol, and the resulting solution was serially diluted to prepare a standard sample. The standard sample having a predetermined concentration was added to the sample, and adsorption onto SPME fiber was performed in the same manner as with the sample alone, followed by GC/MS measurement. The peak area of an ion at m/z 151 was used for quantification.

Reagents used in Examples of the present invention are as described below.
  Catechin reagent I: Teavigo, Taiyo Kagaku Co., Ltd., purity of non-polymer catechins: 94 mass %, ratio of gallate forms:100%
  Catechin reagent II: Catechin hydrate, Cayman Chemical Co., Ltd., purity of non-polymer catechins: 98 mass %, ratio of gallate forms:0%
  Rutin reagent: FUJIFILM Wako Pure Chemical Corporation, rutin purity: 95 mass %
  Astragalin reagent: Kaempferol 3-beta-D-glucopyranoside, Sigma-Aldrich Japan G.K., astragalin purity: 97 mass %
  Excipient: Sandec #100, Sanwa Starch Co., Ltd.

Production Example 1

Production of Green Tea Powder

Third-picked sencha leaves (blend of leaves produced in Miyazaki Prefecture and Kagoshima Prefecture) were ground in a stone mill to obtain green tea powder having an average particle size of 20 µm. The obtained green tea powder had a content of the non-polymer catechins of 11.1 mass %.

Example 1

10 Parts by mass of the catechin reagent I, 0.20 part by mass of the rutin reagent, and 0.010 part by mass of the astragalin reagent were added together, and lastly, the excipient was added thereto so as to adjust a total amount to 100 parts by mass. After homogeneous mixing, 1 g of the mixture was subjected to stickpack to obtain a stick instant beverage. The obtained stick instant beverage was analyzed, and the sensory evaluation was conducted by a method described below. The results are shown in Table 1. The contents of the obtained stick instant beverage had solids content of 97.0 mass %.

Examples 2 to 5

Stick instant beverages were obtained by the same operations as those of Example 1, except that the blending amount of the astragalin reagent was changed. Each of the obtained stick instant beverages was subjected to analysis and sensory evaluation in the same manner as in Example 1. The results are shown in Table 1. The contents of each of the obtained stick instant beverages had solids content of 97.0 mass %.

Comparative Example 1

A stick instant beverage was obtained by the same operations as those of Example 1, except that the astragalin reagent was not blended. The obtained stick instant beverage was subjected to analysis and sensory evaluation in the same manner as in Example 1. The results are shown in Table 1. The contents of the obtained stick instant beverage had solids content of 97.0 mass %.

Reference Example 1

A stick instant beverage was obtained by the same operations as those of Example 1, except that the rutin reagent and the astragalin reagent were not blended. The obtained stick instant beverage was subjected to analysis and sensory evaluation in the same manner as in Example 1. The results are shown in Table 1. The contents of the obtained stick instant beverage had solids content of 97.0 mass %.

Sensory Evaluation 1 The stick instant beverage (contents: 1 g) obtained in each of the above-mentioned Examples, Comparative Example, and Reference Example was diluted with 100 mL of hot water at 80° C. to prepare each reconstituted beverage, and four expert panelists performed a sensory test for "bitterness" at a time when each reconstituted beverage was drunk. The sensory test was performed when each panelist had agreed to use evaluation criteria described below as evaluation criteria for the "bitterness". Then, the average of scores given by the expert panelists was determined. The average of the scores is rounded to the first decimal place.

Evaluation Criteria for Bitterness

In the drinking test, evaluation was performed relative to the reconstituted beverage of Reference Example 1 serving as a standard, in accordance with the criteria described below.

Evaluation Criteria for Bitterness

Score 1: The bitterness is stronger than that of the standard.
2: The bitterness is slightly stronger than that of the standard.
3: The bitterness is comparable to that of the standard (Reference Example 1).
4: The bitterness is slightly weaker than that of the standard.
5: The bitterness is weaker than that of the standard.

Example 6

A stick instant beverage was obtained by the same operations as those of Example 1, except that the blending amount of the catechin reagent I was changed. The obtained stick instant beverage was analyzed in the same manner as in Example 1, and the sensory evaluation was conducted by a method described below. The results are shown in Table 2. The contents of the obtained stick instant beverage had solids content of 97.0 mass %.

Example 7

A stick instant beverage was obtained by the same operations as those of Example 2, except that the blending amount of the catechin reagent I was changed. The obtained stick instant beverage was subjected to analysis and sensory evaluation in the same manner as in Example 6. The results are shown in Table 2. The contents of the obtained stick instant beverage had solids content of 97.0 mass %.

Example 8

A stick instant beverage was obtained by the same operations as those of Example 3, except that the blending amount of the catechin reagent I was changed. The obtained stick instant beverage was subjected to analysis and sensory evaluation in the same manner as in Example 6. The results are shown in Table 2. The contents of the obtained stick instant beverage had solids content of 97.0 mass %.

Comparative Example 2

A stick instant beverage was obtained by the same operations as those of Comparative Example 1, except that the blending amount of the catechin reagent I was changed. The obtained stick instant beverage was subjected to analysis and sensory evaluation in the same manner as in Example 6. The results are shown in Table 2. The contents of the obtained stick instant beverage had solids content of 97.0 mass %.

Reference Example 2

A stick instant beverage was obtained by the same operations as those of Reference Example 1, except that the blending amount of the catechin reagent I was changed. The obtained stick instant beverage was subjected to analysis and sensory evaluation in the same manner as in Example 6. The results are shown in Table 2. The contents of the obtained stick instant beverage had solids content of 97.0 mass %.

TABLE 1

|  |  |  | Example 1 | Example 2 | Example 3 | Example 4 | Example 5 | Comparative Example 1 | Reference Example 1 |
|---|---|---|---|---|---|---|---|---|---|
| Analysis value or calculated value (solids) | (A) Non-polymer catechins | mass % | 9.4 | 9.4 | 9.4 | 9.4 | 9.4 | 9.4 | 9.4 |
|  | (B) Rutin | mass % | 0.19 | 0.19 | 0.19 | 0.19 | 0.19 | 0.19 | — |
|  | (C) Astragalin | mass % | 0.010 | 0.030 | 0.10 | 0.19 | 0.39 | — | — |
|  | Mass ratio [(B)/(A)] [×10$^{-2}$][1] | [—] | 2.0 | 2.0 | 2.0 | 2.0 | 2.0 | 2.0 | — |
|  | Mass ratio [(C)/(A)] [×10$^{-3}$][2] | [—] | 1.1 | 3.2 | 11 | 20 | 41 | — | — |
| Evaluation |  | Bitterness | 3.0 | 3.5 | 4.5 | 4.3 | 3.8 | 1.0 | 3.0 |

[1] Values obtained by multiplying the values in the table by $10^{-2}$
[2] Values obtained by multiplying the values in the table by $10^{-3}$ Sensory Evaluation 2 The stick instant beverage obtained in each of the above-mentioned Examples, Comparative Example, and Reference Example was prepared into a reconstituted beverage by the same method as that of Sensory Evaluation 1. Then, each reconstituted beverage was evaluated by four expert panelists, who had agreed to perform the evaluation on the same five-point scale as that of Sensory Evaluation 1, except that the evaluation was performed relative to the reconstituted beverage of Reference Example 2 serving as a standard. Then, the average of scores given by the expert panelists was determined. The average of the scores is rounded to the first decimal place.

TABLE 2

|  |  |  | Example 6 | Example 7 | Example 8 | Comparative Example 2 | Reference Example 2 |
|---|---|---|---|---|---|---|---|
| Analysis value or calculated value (solids) | (A) Non-polymer catechins | mass % | 2.8 | 2.8 | 2.8 | 2.8 | 2.8 |
|  | (B) Rutin | mass % | 0.19 | 0.19 | 0.19 | 0.19 | — |
|  | (C) Astragalin | mass % | 0.010 | 0.029 | 0.10 | — | — |
|  | Mass ratio [(B)/(A)] [×10$^{-2}$]$^{1)}$ | [—] | 6.8 | 6.8 | 6.8 | 6.8 | — |
|  | Mass ratio [(C)/(A)] [×10$^{-3}$]$^{2)}$ | [—] | 3.6 | 11 | 36 | — | — |
| Evaluation | Bitterness |  | 3.3 | 4.0 | 4.0 | 1.0 | 3.0 |

$^{1)}$Values obtained by multiplying the values in the table by $10^{-2}$
$^{2)}$Values obtained by multiplying the values in the table by $10^{-3}$ Example 9

A stick instant beverage was obtained by the same operations as those of Example 1, except that 7 parts by mass of the catechin reagent I, 0.20 part by mass of the rutin reagent, and 0.07 part by mass of the astragalin reagent were added together, and lastly, the excipient was added thereto so as to adjust a total amount to 100 parts by mass. The obtained stick instant beverage was analyzed in the same manner as in Example 1, and the sensory evaluation was conducted by a method described below. The results are shown in Table 3. The contents of the obtained stick instant beverage had solids content of 97.0 mass %.

Comparative Example 3

A stick instant beverage was obtained by the same operations as those of Example 9, except that the astragalin reagent was not blended. The obtained stick instant beverage was subjected to analysis and sensory evaluation in the same manner as in Example 9. The results are shown in Table 3. The contents of the obtained stick instant beverage had solids content of 97.0 mass %.

Reference Example 3

A stick instant beverage was obtained by the same operations as those of Example 9, except that the rutin reagent and the astragalin reagent were not blended. The obtained stick instant beverage was subjected to analysis and sensory evaluation in the same manner as in Example 9. The results are shown in Table 3. The contents of the obtained stick instant beverage had solids content of 97.0 mass %.

Sensory Evaluation 3
The stick instant beverage obtained in each of the above-mentioned Example, Comparative Example, and Reference Example was prepared into a reconstituted beverage by the same method as that of Sensory Evaluation 1. Then, each reconstituted beverage was evaluated by four expert panelists, who had agreed to perform the evaluation on the same five-point scale as that of Sensory Evaluation 1, except that the evaluation was performed relative to the reconstituted beverage of Reference Example 3 serving as a standard. Then, the average of scores given by the expert panelists was determined. The average of the scores is rounded to the first decimal place.

TABLE 3

|  |  |  | Example 9 | Comparative Example 3 | Reference Example 3 |
|---|---|---|---|---|---|
| Analysis value or calculated value (solids) | (A) Non-polymer catechins | mass % | 6.6 | 6.6 | 6.6 |
|  | (B) Rutin | mass % | 0.19 | 0.19 | — |
|  | (C) Astragalin | mass % | 0.068 | — | — |
|  | Mass ratio [(B)/(A)][×10$^{-2}$]$^{1)}$ | [—] | 2.9 | 2.9 | — |
|  | Mass ratio [(C)/(A)][×10$^{-3}$]$^{2)}$ | [—] | 11 | — | — |
| Evaluation | Bitterness |  | 4.3 | 1.0 | 3.0 |

$^{1)}$Values obtained by multiplying the values in the table by $10^{-2}$
$^{2)}$Values obtained by multiplying the values in the table by $10^{-3}$ Example 10

A stick instant beverage was obtained by the same operations as those of Example 1, except that 20 parts by mass of the catechin reagent I, 0.20 part by mass of the rutin reagent, and 0.10 part by mass of the astragalin reagent were added together, and lastly, the excipient was added thereto so as to adjust a total amount to 100 parts by mass. The obtained stick instant beverage was analyzed in the same manner as in Example 1, and the sensory evaluation was conducted by a method described below. The results are shown in Table 4. The contents of the obtained stick instant beverage had solids content of 97.0 mass %.

Examples 11 and 12

Stick instant beverages were obtained by the same operations as those of Example 10, except that the blending amount of the astragalin reagent was changed. Each of the obtained stick instant beverages was subjected to analysis and sensory evaluation in the same manner as in Example 10. The results are shown in Table 4. The contents of each of the obtained stick instant beverages had solids content of 97.0 mass %.

Comparative Example 4

A stick instant beverage was obtained by the same operations as those of Example 10, except that the astragalin reagent was not blended. The obtained stick instant beverage was subjected to analysis and sensory evaluation in the same manner as in Example 10. The results are shown in Table 4. The contents of the obtained stick instant beverage had solids content of 97.0 mass %.

Reference Example 4

A stick instant beverage was obtained by the same operations as those of Example 10, except that the rutin reagent and the astragalin reagent were not blended. The obtained stick instant beverage was subjected to analysis and sensory evaluation in the same manner as in Example 10. The results are shown in Table 4. The contents of the obtained stick instant beverage had solids content of 97.0 mass %.

Sensory Evaluation 4

The stick instant beverage obtained in each of the above-mentioned Examples, Comparative Example, and Reference Example was prepared into a reconstituted beverage by the same method as that of Sensory Evaluation 1. Then, each reconstituted beverage was evaluated by four expert panelists, who had agreed to perform the evaluation on the same five-point scale as that of Sensory Evaluation 1, except that the evaluation was performed relative to the reconstituted beverage of Reference Example 4 serving as a standard. Then, the average of scores given by the expert panelists was determined. The average of the scores is rounded to the first decimal place.

TABLE 4

| | | | Example 10 | Example 11 | Example 12 | Comparative Example 4 | Reference Example 4 |
|---|---|---|---|---|---|---|---|
| Analysis value or calculated value (solids) | (A) Non-polymer catechins | mass % | 19 | 19 | 19 | 19 | 19 |
| | (B) Rutin | mass % | 0.19 | 0.19 | 0.19 | 0.19 | — |
| | (C) Astragalin | mass % | 0.10 | 0.19 | 0.39 | — | — |
| | Mass ratio [(B)/(A)] [×10$^{-2}$][1) | [—] | 1.0 | 1.0 | 1.0 | 1.0 | — |
| | Mass ratio [(C)/(A)] [×10$^{-3}$][2) | [—] | 5.3 | 10 | 21 | — | — |
| Evaluation | Bitterness | | 4.3 | 4.3 | 4.0 | 1.0 | 3.0 |

[1)]Values obtained by multiplying the values in the table by $10^{-2}$
[2)]Values obtained by multiplying the values in the table by $10^{-3}$

Examples 13 to 16

Stick instant beverages were obtained by the same operations as those of Example 3, except that the blending amount of the rutin reagent was changed. The obtained stick instant beverages were subjected to analysis and sensory evaluation in the same manner as in Example 3. The results are shown in Table 5 together with the results of Example 3, Comparative Example 1, and Reference Example 1. The contents of each of the obtained stick instant beverages had solids content of 97.0 mass %.

Comparative Example 5

A stick instant beverage was obtained by the same operations as those of Example 13, except that the astragalin reagent was not blended. The obtained stick instant beverage was subjected to analysis and sensory evaluation in the same manner as in Example 3. The results are shown in Table 5 together with the results of Example 3, Comparative Example 1, and Reference Example 1. The contents of the obtained stick instant beverage had solids content of 97.0 mass %.

Comparative Example 6

A stick instant beverage was obtained by the same operations as those of Example 14, except that the astragalin reagent was not blended. The obtained stick instant beverage was subjected to analysis and sensory evaluation in the same manner as in Example 3. The results are shown in Table 5 together with the results of Example 3, Comparative Example 1, and Reference Example 1. The contents of the obtained stick instant beverage had solids content of 97.0 mass %.

Comparative Example 7

A stick instant beverage was obtained by the same operations as those of Example 15, except that the astragalin reagent was not blended. The obtained stick instant beverage was subjected to analysis and sensory evaluation in the same manner as in Example 3. The results are shown in Table 5 together with the results of Example 3, Comparative Example 1, and Reference Example 1. The contents of the obtained stick instant beverage had solids content of 97.0 mass %.

Comparative Example 8

A stick instant beverage was obtained by the same operations as those of Example 16, except that the astragalin reagent was not blended. The obtained stick instant beverage was subjected to analysis and sensory evaluation in the same manner as in Example 3. The results are shown in Table 5 together with the results of Example 3, Comparative Example 1, and Reference Example 1. The contents of the obtained stick instant beverage had solids content of 97.0 mass %.

TABLE 5

|  |  |  | Example 3 | Example 13 | Example 14 | Example 15 | Example 16 | Comparative Example 1 | Comparative Example 5 | Comparative Example 6 | Comparative Example 7 | Comparative Example 8 | Reference Example 1 |
|---|---|---|---|---|---|---|---|---|---|---|---|---|---|
| Analysis value or calculated value (solids) | (A) Non-polymer catechins | mass % | 9.4 | 9.4 | 9.4 | 9.4 | 9.4 | 9.4 | 9.4 | 9.4 | 9.4 | 9.4 | 9.4 |
|  | (B) Rutin | mass % | 0.19 | 0.010 | 0.10 | 0.38 | 0.76 | 0.19 | 0.010 | 0.10 | 0.38 | 0.76 | — |
|  | (C) Astragalin | mass % | 0.10 | 0.10 | 0.10 | 0.10 | 0.10 | — | — | — | — | — | — |
|  | Mass ratio [(B)/(A)] [×10$^{-2}$]$^{1)}$ | [—] | 2.0 | 0.10 | 1.1 | 4.0 | 8.1 | 2.0 | 0.10 | 1.1 | 4.0 | 8.1 | — |
|  | Mass ratio [(C)/(A)] [×10$^{-3}$]$^{2)}$ | [—] | 11 | 11 | 11 | 11 | 11 | — | — | — | — | — | — |
| Evaluation | Bitterness |  | 4.5 | 4.5 | 4.5 | 4.5 | 4.5 | 1.0 | 2.8 | 1.3 | 1.0 | 1.0 | 3.0 |
|  | Note |  |  |  |  | An astringent taste is slightly sensed. | An astringent taste is strongly sensed. |  |  |  | An astringent taste is slightly sensed. | An astringent taste is strongly sensed. |  |

$^{1)}$Values obtained by multiplying the values in the table by $10^{-2}$
$^{2)}$Values obtained by multiplying the values in the table by $10^{-3}$ Examples 17 and 18

Stick instant beverages were obtained by the same operations as those of Example 8, except that the blending amount of the rutin reagent was changed. The obtained stick instant beverages were subjected to analysis and sensory evaluation in the same manner as in Example 8. The results are shown in Table 6 together with the results of Example 8, Comparative Example 2, and Reference Example 2. The contents of each of the obtained stick instant beverages had solids content of 97.0 mass %.

Comparative Example 9

A stick instant beverage was obtained by the same operations as those of Example 17, except that the astragalin reagent was not blended. The obtained stick instant beverage was subjected to analysis and sensory evaluation in the same manner as in Example 8. The results are shown in Table 6 together with the results of Example 8, Comparative Example 2, and Reference Example 2. The contents of the obtained stick instant beverage had solids content of 97.0 mass %.

Comparative Example 10

A stick instant beverage was obtained by the same operations as those of Example 18, except that the astragalin reagent was not blended. The obtained stick instant beverage was subjected to analysis and sensory evaluation in the same manner as in Example 8. The results are shown in Table 6 together with the results of Example 8, Comparative Example 2, and Reference Example 2. The contents of the obtained stick instant beverage had solids content of 97.0 mass %.

TABLE 6

|  |  |  | Example 8 | Example 17 | Example 18 | Comparative Example 2 | Comparative Example 9 | Comparative Example 10 | Reference Example 2 |
|---|---|---|---|---|---|---|---|---|---|
| Analysis value or calculated value (solids) | (A) Non-polymer catechins | mass % | 2.8 | 2.8 | 2.8 | 2.8 | 2.8 | 2.8 | 2.8 |
|  | (B) Rutin | mass % | 0.19 | 0.01 | 0.06 | 0.19 | 0.01 | 0.06 | — |
|  | (C) Astragalin | mass % | 0.10 | 0.10 | 0.10 | — | — | — | — |
|  | Mass ratio [(B)/(A)] [×10$^{-2}$]$^{1)}$ | [—] | 6.8 | 0.36 | 2.1 | 6.8 | 0.36 | 2.1 | — |
|  | Mass ratio [(C)/(A)] [×10$^{-3}$]$^{2)}$ | [—] | 36 | 36 | 36 | — | — | — | — |
| Evaluation | Bitterness |  | 4.0 | 4.0 | 4.0 | 1.0 | 2.8 | 1.8 | 3.0 |

$^{1)}$Values obtained by multiplying the values in the table by $10^{-2}$
$^{2)}$Values obtained by multiplying the values in the table by $10^{-3}$ Examples 19 to 22

Stick instant beverages were obtained by the same operations as those of Example 3, except that a vanillin reagent was further blended. The obtained stick instant beverages were subjected to analysis and sensory evaluation in the same manner as in Example 3. The results are shown in Table 7 together with the results of Example 3, Comparative Example 1, and Reference Example 1. The contents of each of the obtained stick instant beverages had solids content of 97.0 mass %.

TABLE 7

|  |  |  | Example 3 | Example 19 | Example 20 | Example 21 | Example 22 | Comparative Example 1 | Reference Example 1 |
|---|---|---|---|---|---|---|---|---|---|
| Analysis value or calculated value (solids) | (A) Non-polymer catechins | mass % | 9.4 | 9.4 | 9.4 | 9.4 | 9.4 | 9.4 | 9.4 |
|  | (B) Rutin | mass % | 0.19 | 0.19 | 0.19 | 0.19 | 0.19 | 0.19 | — |
|  | (C) Astragalin | mass % | 0.10 | 0.10 | 0.10 | 0.10 | 0.10 | — | — |
|  | (D) Vanillin | mass % [×10$^{-4}$]$^{3)}$ | — | 0.30 | 1.0 | 10 | 50 | — | — |
|  | Mass ratio [(B)/(A)] [×10$^{-2}$]$^{1)}$ | [—] | 2.0 | 2.0 | 2.0 | 2.0 | 2.0 | 2.0 | — |
|  | Mass ratio [(C)/(A)] [×10$^{-3}$]$^{2)}$ | [—] | 11 | 11 | 11 | 11 | 11 | — | — |
| Evaluation |  | Bitterness | 4.5 | 4.8 | 5.0 | 5.0 | 5.0 | 1.0 | 3.0 |
|  |  | Note |  |  |  | A sweet aroma is slightly sensed. | A sweet aroma is sensed. |  |  |

$^{1)}$Values obtained by multiplying the values in the table by 10$^{-2}$
$^{2)}$Values obtained by multiplying the values in the table by 10$^{-3}$
$^{3)}$Values obtained by multiplying the values in the table by 10$^{-4}$ Examples 23 to 26

Stick instant beverages were obtained by the same operations as those of Example 3, except that the catechin reagent II was further blended in addition to the catechin reagent I to achieve a ratio of gallate forms shown in Table 8. The obtained stick instant beverages were subjected to analysis and sensory evaluation in the same manner as in Example 3. The results are shown in Table 8. The contents of each of the obtained stick instant beverages had solids content of 97.0 mass %.

Comparative Examples 11 to 14

Stick instant beverages were obtained by the same operations as those of Examples 23 to 26, except that the astragalin reagent was not blended. The obtained stick instant beverages were subjected to analysis and sensory evaluation in the same manner as in Example 3. The results are shown in Table 8. The contents of each of the obtained stick instant beverages had solids content of 97.0 mass %.

Reference Example 5

A stick instant beverage was obtained by the same operations as those of Example 26, except that the rutin reagent and the astragalin reagent were not blended. The obtained stick instant beverage was subjected to analysis and sensory evaluation in the same manner as in Example 3. The results are shown in Table 8. The contents of the obtained stick instant beverage had solids content of 97.0 mass %.

TABLE 8

|  |  |  | Example 3 | Example 23 | Example 24 | Example 25 | Example 26 | Comparative Example 1 | Comparative Example 11 | Comparative Example 12 | Comparative Example 13 | Comparative Example 14 | Reference Example 1 | Reference Example 5 |
|---|---|---|---|---|---|---|---|---|---|---|---|---|---|---|
| Analysis value or calculated value (solids) | (A) Non-polymer catechins | mass % | 9.4 | 9.4 | 9.4 | 9.4 | 9.4 | 9.4 | 9.4 | 9.4 | 9.4 | 9.4 | 9.4 | 9.4 |
|  | (B) Rutin | mass % | 0.19 | 0.19 | 0.19 | 0.19 | 0.19 | 0.19 | 0.19 | 0.19 | 0.19 | 0.19 | — | — |
|  | (C) Astragalin | mass % | 0.10 | 0.10 | 0.10 | 0.10 | 0.10 | — | — | — | — | — | — | — |
|  | Mass ratio [(B)/(A)] [×10$^{-2}$]$^{1)}$ | [—] | 2.0 | 2.0 | 2.0 | 2.0 | 2.0 | 2.0 | 2.0 | 2.0 | 2.0 | 2.0 | — | — |

TABLE 8-continued

|  |  |  | Example 3 | Example 23 | Example 24 | Example 25 | Example 26 | Comparative Example 1 | Comparative Example 11 | Comparative Example 12 | Comparative Example 13 | Comparative Example 14 | Reference Example 1 | Reference Example 5 |
|---|---|---|---|---|---|---|---|---|---|---|---|---|---|---|
|  | Mass ratio [(C)/(A)] [×10⁻³]²⁾ | [—] | 11 | 11 | 11 | 11 | 11 | — | — | — | — | — | — | — |
|  | Ratio of gallate forms | [%] | 100 | 80 | 70 | 60 | 50 | 100 | 80 | 70 | 60 | 50 | 100 | 50 |
| Evaluation | Bitterness |  | 4.0 | 4.0 | 4.5 | 4.8 | 5.0 | 1.0 | 1.0 | 1.3 | 1.3 | 1.3 | 3.0 | 4.3 |

1) Values obtained by multiplying the values in the table by $10^{-2}$
2) Values obtained by multiplying the values in the table by $10^{-3}$ Example 27

10 Parts by mass of the catechin reagent I, 0.20 part by mass of the rutin reagent, 0.010 part by mass of the astragalin reagent, and 2 parts by mass of calcium stearate were added together, and lastly, the excipient was added so as to adjust a total amount to 100 parts by mass, followed by homogeneous mixing. Then, the mixture was tableted at a mass of 1 g per tablet using a single-punch tableting machine (manufactured by RIKEN) with a ring-shaped punch having a hole diameter of 14 mm to obtain a circular tablet. The obtained tablet was analyzed, and the sensory evaluation was conducted by a method described below. The results are shown in Table 9. The obtained tablet had solids content of 97.0 mass %.

Comparative Example 15

A tablet was obtained by the same operations as those of Example 27, except that the astragalin reagent was not blended. The obtained tablet was subjected to analysis and sensory evaluation in the same manner as in Example 27. The results are shown in Table 9. The obtained tablet had solids content of 97.0 mass %.

Reference Example 6

A tablet was obtained by the same operations as those of Example 27, except that the rutin reagent and the astragalin reagent were not blended. The obtained tablet was subjected to analysis and sensory evaluation in the same manner as in Example 27. The results are shown in Table 9. The obtained tablet had solids content of 97.0 mass %.

Sensory Evaluation 5

One tablet obtained in each of the above-mentioned Example, Comparative Example, and Reference Example was held in the mouth without water and then immediately chewed up, and four expert panelists performed a sensory test for "bitterness" at a time when the tablet completely disappeared due to saliva in the mouth. The sensory test was performed when the four expert panelists had agreed to perform evaluation on the same five-point scale as that of Sensory Evaluation 1, except that the evaluation was performed relative to the tablet of Reference Example 6 serving as a standard. Then, the average of scores given by the expert panelists was determined. The average of the scores is rounded to the first decimal place.

TABLE 9

|  |  |  | Example 27 | Comparative Example 15 | Reference Example 6 |
|---|---|---|---|---|---|
| Analysis value or calculated value (solids) | (A) Non-polymer catechins | mass % | 9.4 | 9.4 | 9.4 |
|  | (B) Rutin | mass % | 0.19 | 0.19 | — |
|  | (C) Astragalin | mass % | 0.10 | — | — |
|  | Mass ratio [(B)/(A)][×10⁻²]¹⁾ | [—] | 2.0 | 2.0 | — |
|  | Mass ratio [(C)/(A)][×10⁻³]²⁾ | [—] | 10 | — | — |
| Evaluation | Bitterness |  | 4.0 | 1.0 | 3.0 |

1) Values obtained by multiplying the values in the table by $10^{-2}$
2) Values obtained by multiplying the values in the table by $10^{-3}$ Example 28

A stick instant beverage was obtained by the same operations as those of Example 1, except that 15 parts by mass of the green tea powder obtained in Production Example 1, 8.2 parts by mass of the catechin reagent I, 0.18 part by mass of the rutin reagent, and 0.10 part by mass of the astragalin reagent were added together, and lastly, the excipient was added thereto so as to adjust a total amount to 100 parts by mass. The obtained stick instant beverage was analyzed in the same manner as in Example 1, and the sensory evaluation was conducted by a method described below. The results are shown in Table 10. The contents of the obtained stick instant beverage had solids content of 97.0 mass %.

Example 29

A stick instant beverage was obtained by the same operations as those of Example 28, except that a vanillin reagent was further blended. The obtained stick instant beverage was subjected to analysis and sensory evaluation in the same manner as in Example 28. The results are shown in Table 10. The contents of the obtained stick instant beverage had solids content of 97.0 mass %.

Comparative Example 16

A stick instant beverage was obtained by the same operations as those of Example 28, except that the astragalin reagent was not blended. The obtained stick instant beverage was subjected to analysis and sensory evaluation in the same manner as in Example 28. The results are shown in Table 10. The contents of the obtained stick instant beverage had solids content of 97.0 mass %.

Reference Example 7

A stick instant beverage was obtained by the same operations as those of Example 28, except that the rutin reagent and the astragalin reagent were not blended. The obtained stick instant beverage was subjected to analysis and sensory evaluation in the same manner as in Example 28. The results are shown in Table 10. The contents of the obtained stick instant beverage had solids content of 97.0 mass %.

Sensory Evaluation 6

The stick instant beverage obtained in each of the above-mentioned Examples, Comparative Example, and Reference Example was prepared into a reconstituted beverage by the same method as that of Sensory Evaluation 1. Then, each reconstituted beverage was evaluated by four expert panelists, who had agreed to perform the evaluation on the same five-point scale as that of Sensory Evaluation 1, except that the evaluation was performed relative to the reconstituted beverage of Reference Example 7 serving as a standard. Then, the average of scores given by the expert panelists was determined. The average of the scores is rounded to the first decimal place.

TABLE 10

| | | | Example 28 | Example 29 | Comparative Example 16 | Reference Example 7 |
|---|---|---|---|---|---|---|
| Analysis value or calculated value (solids) | (A) Non-polymer catechins | mass % | 9.4 | 9.4 | 9.4 | 9.4 |
| | (B) Rutin | mass % | 0.19 | 0.19 | 0.19 | 0.021 |
| | (C) Astragalin | mass % | 0.090 | 0.090 | 0.00051 | 0.00051 |
| | (D) Vanillin | mass % $[\times 10^{-4}]^{3)}$ | 0.083 | 1.0 | 0.083 | 0.083 |
| | Mass ratio [(B)/(A)] $[\times 10^{-2}]^{1)}$ | [—] | 2.0 | 2.0 | 2.0 | 0.22 |
| | Mass ratio [(C)/(A)] $[\times 10^{-3}]^{2)}$ | [—] | 10 | 10 | 0.054 | 0.054 |
| Evaluation | Bitterness | | 4.5 | 5.0 | 1.0 | 3.0 |
| | Note | | Aroma release from green tea is good. | Aroma release from green tea is good. | | |

$^{1)}$Values obtained by multiplying the values in the table by $10^{-2}$
$^{2)}$Values obtained by multiplying the values in the table by $10^{-3}$
$^{3)}$Values obtained by multiplying the values in the table by $10^{-4}$ Example 30

97.3 Parts by mass of white chocolate (Meiji Co., Ltd., Meiji White Chocolate), 2.1 parts by mass of the catechin reagent I, 0.036 part by mass of the rutin reagent, and 0.024 part by mass of the astragalin reagent were placed in a 1 L container, and homogeneously mixed in a warm bath of warm water at 60° C. Next, while being mixed with a rubber spatula, the chocolate was slowly cooled in a warm bath of warm water at 33° C. When the temperature of the chocolate reached 34° C., 0.49 part by mass of a seed (Fuji Oil Co., Ltd., Chocoseed A) was added thereto and mixed therewith, and lastly, the chocolate was poured into a chocolate mold and left at rest in a thermostatic chamber at 15° C. to harden the chocolate. The obtained chocolate was analyzed, and the sensory evaluation was conducted by a method described below. The results are shown in Table 11. The obtained chocolate had solids content of 99.0 mass %.

Example 31

Chocolate was obtained by the same operations as those of Example 30, except that the blending amount of the astragalin reagent was changed. The obtained chocolate was subjected to analysis and sensory evaluation in the same manner as in Example 30. The results are shown in Table 11. The obtained chocolate had solids content of 99.0 mass %.

Comparative Example 17

Chocolate was obtained by the same operations as those of Example 30, except that the astragalin reagent was not blended. The obtained chocolate was subjected to analysis and sensory evaluation in the same manner as in Example 30. The results are shown in Table 11. The obtained chocolate had solids content of 99.0 mass %.

Reference Example 8

Chocolate was obtained by the same operations as those of Example 30, except that the rutin reagent and the astragalin reagent were not blended. The obtained chocolate was subjected to analysis and sensory evaluation in the same manner as in Example 30. The results are shown in Table 11. The obtained chocolate had solids content of 99.0 mass %.

Sensory Evaluation 7

5 g of the chocolate obtained in each of the above-mentioned Examples, Comparative Example, and Reference Example was held in the mouth, and then four expert panelists performed a sensory test for "bitterness" at a time when the chocolate completely disappeared by being dissolved by saliva in the mouth. The sensory test was performed when the four expert panelists had agreed to perform evaluation on the same five-point scale as that of Sensory Evaluation 1, except that the evaluation was performed relative to the chocolate of Reference Example 8 serving as a standard. Then, the average of scores given by the expert panelists was determined. The average of the scores is rounded to the first decimal place.

TABLE 11

| | | | Example 30 | Example 31 | Comparative Example 17 | Reference Example 8 |
|---|---|---|---|---|---|---|
| Analysis value or calculated value (solids) | (A) Non-polymer catechins | mass % | 2.0 | 2.0 | 2.0 | 2.0 |
| | (B) Rutin | mass % | 0.035 | 0.035 | 0.035 | — |
| | (C) Astragalin | mass % | 0.024 | 0.0050 | — | — |
| | Mass ratio [(B)/(A)] [×10$^{-2}$]$^{1)}$ | [—] | 1.8 | 1.8 | 1.8 | — |
| | Mass ratio [(C)/(A)] [×10$^{-3}$]$^{2)}$ | [—] | 12 | 2.5 | — | — |
| Evaluation | Bitterness | | 4.0 | 3.8 | 1.0 | 3.0 |

$^{1)}$Values obtained by multiplying the values in the table by $10^{-2}$
$^{2)}$Values obtained by multiplying the values in the table by $10^{-3}$ Example 32

Chocolate was obtained by the same operations as those of Example 30, except that the blending amounts of the catechin reagent I, the rutin reagent, and the astragalin reagent were changed. The obtained chocolate was analyzed in the same manner as in Example 30, and the sensory evaluation was conducted by a method described below. The results are shown in Table 12. The obtained chocolate had solids content of 99.0 mass %.

Comparative Example 18

Chocolate was obtained by the same operations as those of Example 32, except that the astragalin reagent was not blended. The obtained chocolate was subjected to analysis and sensory evaluation in the same manner as in Example 32. The results are shown in Table 12. The obtained chocolate had solids content of 99.0 mass %.

Reference Example 9

Chocolate was obtained by the same operations as those of Example 32, except that the rutin reagent and the astragalin reagent were not blended. The obtained chocolate was subjected to analysis and sensory evaluation in the same manner as in Example 32. The results are shown in Table 12. The obtained chocolate had solids content of 99.0 mass %.

Sensory Evaluation 8

Evaluation was performed in the same manner as in Sensory Evaluation 7, except that the evaluation was performed relative to the chocolate of Reference Example 9 serving as a standard.

TABLE 12

| | | | Example 32 | Comparative Example 18 | Reference Example 9 |
|---|---|---|---|---|---|
| Analysis value or calculated value (solids) | (A) Non-polymer catechins | mass % | 4.0 | 4.0 | 4.0 |
| | (B) Rutin | mass % | 0.070 | 0.070 | — |
| | (C) Astragalin | mass % | 0.048 | — | — |
| | Mass ratio [(B)/(A)][×10$^{-2}$]$^{1)}$ | [—] | 1.8 | 1.8 | — |
| | Mass ratio [(C)/(A)][×10$^{-3}$]$^{2)}$ | [—] | 12 | — | — |
| Evaluation | Bitterness | | 4.0 | 1.0 | 3.0 |

$^{1)}$Values obtained by multiplying the values in the table by $10^{-2}$
$^{2)}$Values obtained by multiplying the values in the table by $10^{-3}$ Example 33

A baked confection was prepared by a method described below using raw materials in amounts shown below.

1) 16.8 Parts by mass of shortening, 15.8 parts by mass of caster sugar, 0.50 part by mass of table salt, 2.6 parts by mass of the catechin reagent I, 0.049 part by mass of the rutin reagent, and 0.036 part by mass of the astragalin reagent were weighed, and then placed in a mixer (N50 MIXER (5-quart mixer) manufactured by Hobart). The contents were stirred at medium speed until the specific gravity thereof reached 0.70, to prepare a sugar batter.
2) While the sugar batter obtained in 1) above was stirred at medium speed, egg water obtained by mixing 3.2 parts by mass of whole egg with 8.2 parts by mass of water was added in small portions thereto over 75 seconds.
3) To the mixture obtained in 2) above, 52.6 parts by mass of weak flour was added, and the whole was stirred at low speed for 30 seconds and then at medium speed for 15 seconds to prepare a dough.
4) The dough obtained in 3) above was prepared into a biscuit dough using a cutting die (diameter: about 3.5 mm, dough thickness: 4 mm).
5) The biscuit dough was baked in an oven (upper fire: 200° C./lower fire: 180° C.) for 9 minutes.
6) After the baking, the baked product was removed from the oven, placed on a mesh, and cooled under room temperature for 10 minutes. After that, the resultant was put into a polyethylene bag with a zipper, and left to stand in a thermostatic chamber at 20° C. overnight to obtain a biscuit.

The obtained biscuit was analyzed, and the sensory evaluation was conducted by a method described below. The results are shown in Table 13. The obtained biscuit had solids content of 98.9 mass %.

Example 34

A biscuit was obtained by the same operations as those of Example 33, except that the blending amount of the astragalin reagent was changed. The obtained biscuit was subjected to analysis and sensory evaluation in the same manner as in Example 33. The results are shown in Table 13. The obtained biscuit had solids content of 98.9 mass %.

Comparative Example 19

A biscuit was obtained by the same operations as those of Example 33, except that the astragalin reagent was not blended. The obtained biscuit was subjected to analysis and sensory evaluation in the same manner as in Example 33. The results are shown in Table 13. The obtained biscuit had solids content of 98.9 mass %.

Reference Example 10

A biscuit was obtained by the same operations as those of Example 33, except that the rutin reagent and the astragalin reagent were not blended. The obtained biscuit was subjected to analysis and sensory evaluation in the same manner as in Example 33. The results are shown in Table 13. The obtained biscuit had solids content of 98.9 mass %.

Sensory Evaluation 9

The biscuit obtained in each of the above-mentioned Examples, Comparative Example, and Reference Example was held in the mouth and chewed up, and four expert panelists performed a sensory test for "bitterness" at a time when the biscuit completely disappeared by being melted by saliva in the mouth. The sensory test was performed when the four expert panelists had agreed to perform evaluation on the same five-point scale as that of Sensory Evaluation 1, except that the evaluation was performed relative to the biscuit of Reference Example 10 serving as a standard. Then, the average of scores given by the expert panelists was determined. The average of the scores is rounded to the first decimal place.

TABLE 13

|  |  |  | Example 33 | Example 34 | Comparative Example 19 | Reference Example 10 |
|---|---|---|---|---|---|---|
| Analysis value or calculated value (solids) | (A) Non-polymer catechins | mass % | 2.8 | 2.8 | 2.8 | 2.8 |
|  | (B) Rutin | mass % | 0.047 | 0.047 | 0.047 | — |
|  | (C) Astragalin | mass % | 0.034 | 0.0070 | — | — |
|  | Mass ratio [(B)/(A)] [×10$^{-2}$]$^{1)}$ | [—] | 1.7 | 1.7 | 1.7 | — |
|  | Mass ratio [(C)/(A)] [×10$^{-3}$]$^{2)}$ | [—] | 12 | 2.5 | — | — |
| Evaluation | Bitterness |  | 3.0 | 3.0 | 1.0 | 3.0 |

[1] Values obtained by multiplying the values in the table by $10^{-2}$

[2] Values obtained by multiplying the values in the table by $10^{-3}$

Example 35

A biscuit was obtained by the same operations as those of Example 33, except that the blending amounts of the catechin reagent I, the rutin reagent, and the astragalin reagent were changed. The obtained biscuit was analyzed in the same manner as in Example 33, and the sensory evaluation was conducted by a method described below. The results are shown in Table 14. The obtained biscuit had solids content of 98.9 mass %.

Comparative Example 20

A biscuit was obtained by the same operations as those of Example 35, except that the astragalin reagent was not blended. The obtained biscuit was subjected to analysis and sensory evaluation in the same manner as in Example 35. The results are shown in Table 14. The obtained biscuit had solids content of 98.9 mass %.

Reference Example 11

A biscuit was obtained by the same operations as those of Example 35, except that the rutin reagent and the astragalin reagent were not blended. The obtained biscuit was subjected to analysis and sensory evaluation in the same manner as in Example 35. The results are shown in Table 14. The obtained biscuit had solids content of 98.9 mass %.

Sensory Evaluation 10

Evaluation was performed in the same manner as in Sensory Evaluation 9, except that the evaluation was performed relative to the biscuit of Reference Example 11 serving as a standard.

TABLE 14

|  |  |  | Example 35 | Comparative Example 20 | Reference Example 11 |
|---|---|---|---|---|---|
| Analysis value or calculated value (solids) | (A) Non-polymer catechins | mass % | 4.0 | 4.0 | 4.0 |
|  | (B) Rutin | mass % | 0.066 | 0.066 | — |
|  | (C) Astragalin | mass % | 0.048 | — | — |
|  | Mass ratio [(B)/(A)] [×10⁻²]$^{1)}$ | [—] | 1.7 | 1.7 | — |
|  | Mass ratio [(C)/(A)] [×10⁻³]$^{2)}$ | [—] | 12 | — | — |
| Evaluation | Bitterness |  | 3.0 | 1.0 | 3.0 |

$^{1)}$Values obtained by multiplying the values in the table by $10^{-2}$
$^{2)}$Values obtained by multiplying the values in the table by $10^{-3}$

Example 36

A candy was prepared by a method described below.
1) 47.3 parts by mass of starch syrup, 26 parts by mass of granulated sugar, 1.5 parts by mass of trisodium citrate, 0.20 part by mass of a lemon flavor (T. Hasegawa Co., Ltd.), 1.8 parts by mass of the catechin reagent I, 0.030 part by mass of the rutin reagent, and 0.020 part by mass of the astragalin reagent were dissolved in 22.8 parts by mass of water through heating at 70° C. to prepare a liquid candy dough.
2) The liquid candy dough obtained in 1) above was continuously heated at 70° C., and boiled down until its water content was almost completely lost.
3) The liquid candy obtained in 2) above was placed in a mold to be shaped, and cooled at room temperature to obtain a candy.

The obtained candy was subjected to analysis, and subjected to sensory evaluation by a method described below. The results are shown in Table 15. The obtained candy had solids content of 99.0 mass %.

Example 37

A candy was obtained by the same operations as those of Example 36, except that the blending amount of the astragalin reagent was changed. The obtained candy was subjected to analysis and sensory evaluation in the same manner as in Example 36. The results are shown in Table 15. The obtained candy had solids content of 99.0 mass %.

Comparative Example 21

A candy was obtained by the same operations as those of Example 36, except that the astragalin reagent was not blended. The obtained candy was subjected to analysis and sensory evaluation in the same manner as in Example 36. The results are shown in Table 15. The obtained candy had solids content of 99.0 mass %.

Reference Example 12

A candy was obtained by the same operations as those of Example 36, except that the rutin reagent and the astragalin reagent were not blended. The obtained candy was subjected to analysis and sensory evaluation in the same manner as in Example 36. The results are shown in Table 15. The obtained candy had solids content of 99.0 mass %.

Sensory Evaluation 11

The candy obtained in each of the above-mentioned Examples, Comparative Example, and Reference Example was held in the mouth and chewed up, and four expert panelists performed a sensory test for "bitterness" felt while the candy was gradually melted by saliva on the tongue in the mouth. The sensory test was performed when the four expert panelists had agreed to perform evaluation on the same five-point scale as that of Sensory Evaluation 1, except that the evaluation was performed relative to the candy of Reference Example 12 serving as a standard. Then, the average of scores given by the expert panelists was determined. The average of the scores is rounded to the first decimal place.

TABLE 15

|  |  |  | Example 36 | Example 37 | Comparative Example 21 | Reference Example 12 |
|---|---|---|---|---|---|---|
| Analysis value or calculated value | (A) Non-polymer catechins | mass % | 2.1 | 2.1 | 2.1 | 2.1 |
|  | (B) Rutin | mass % | 0.036 | 0.036 | 0.036 | — |
|  | (C) Astragalin | mass % | 0.025 | 0.0052 | — | — |

TABLE 15-continued

|  |  |  | Example 36 | Example 37 | Comparative Example 21 | Reference Example 12 |
|---|---|---|---|---|---|---|
| (solids) | Mass ratio [(B)/(A)] [×10$^{-2}$][1)] | [—] | 1.7 | 1.7 | 1.7 | — |
|  | Mass ratio [(C)/(A)] [×10$^{-3}$][2)] | [—] | 12 | 2.5 | — | — |
| Evaluation | Bitterness |  | 4.0 | 3.5 | 1.0 | 3.0 |

[1)]Values obtained by multiplying the values in the table by 10$^{-2}$
[2)]Values obtained by multiplying the values in the table by 10$^{-3}$ Example 38

A candy was obtained by the same operations as those of Example 36, except that the blending amounts of the catechin reagent I, the rutin reagent, and the astragalin reagent were changed. The obtained candy was analyzed in the same manner as in Example 36, and the sensory evaluation was conducted by a method described below. The results are shown in Table 16. The obtained candy had solids content of 99.0 mass %.

Comparative Example 22

A candy was obtained by the same operations as those of Example 38, except that the astragalin reagent was not blended. The obtained candy was subjected to analysis and sensory evaluation in the same manner as in Example 38. The results are shown in Table 16. The obtained candy had solids content of 99.0 mass %.

Reference Example 13

A candy was obtained by the same operations as those of Example 38, except that the rutin reagent and the astragalin reagent were not blended. The obtained candy was subjected to analysis and sensory evaluation in the same manner as in Example 38. The results are shown in Table 16. The obtained candy had solids content of 99.0 mass %.

Sensory Evaluation 12

Evaluation was performed in the same manner as in Sensory Evaluation 11, except that the evaluation was performed relative to the candy of Reference Example 13 serving as a standard.

TABLE 16

|  |  |  | Example 38 | Comparative Example 22 | Reference Example 13 |
|---|---|---|---|---|---|
| Analysis value or calculated value (solids) | (A) Non-polymer catechins | mass % | 4.0 | 4.0 | 4.0 |
|  | (B) Rutin | mass % | 0.066 | 0.066 | — |
|  | (C) Astragalin | mass % | 0.048 | — | — |
|  | Mass ratio [(B)/(A)][×10$^{-2}$][1)] | [—] | 1.7 | 1.7 | — |
|  | Mass ratio [(C)/(A)][×10$^{-3}$][2)] | [—] | 12 | — | — |
| Evaluation | Bitterness |  | 4.0 | 1.0 | 3.0 |

[1)]Values obtained by multiplying the values in the table by 10$^{-2}$
[2)]Values obtained by multiplying the values in the table by 10$^{-3}$ Example 39

A gummy candy was prepared by a method described below. 1) 7.6 Parts by mass of gelatin, 40 parts by mass of starch syrup, 26 parts by mass of granulated sugar, 1.5 parts by mass of trisodium citrate, 0.20 part by mass of a lemon flavor (T. Hasegawa Co., Ltd.), 2.1 parts by mass of the catechin reagent I, 0.037 part by mass of the rutin reagent, and 0.026 part by mass of the astragalin reagent were dissolved in 22.8 parts by mass of water through heating at 70° C. to prepare a liquid gummy candy dough.
2) The liquid gummy candy dough obtained in 1) above was placed in a mold to be shaped, and allowed to cool at ordinary temperature for 1 hour.
3) The liquid gummy candy dough obtained in 2) above was cooled at 5° C. overnight to obtain a gummy candy.

The obtained gummy candy was analyzed, and the sensory evaluation was conducted by a method described below. The results are shown in Table 17. The obtained gummy candy had solids content of 80.0 mass %.

Example 40

A gummy candy was obtained by the same operations as those of Example 39, except that the blending amount of the astragalin reagent was changed. The obtained gummy candy was subjected to analysis and sensory evaluation in the same manner as in Example 39. The results are shown in Table 17. The obtained gummy candy had solids content of 80.0 mass %.

Comparative Example 23

A gummy candy was obtained by the same operations as those of Example 39, except that the astragalin reagent was not blended. The obtained gummy candy was subjected to analysis and sensory evaluation in the same manner as in Example 39. The results are shown in Table 17. The obtained gummy candy had solids content of 80.0 mass %.

Reference Example 14

A gummy candy was obtained by the same operations as those of Example 39, except that the rutin reagent and the astragalin reagent were not blended. The obtained gummy candy was subjected to analysis and sensory evaluation in the same manner as in Example 39. The results are shown in Table 17. The obtained gummy candy had solids content of 80.0 mass %.

Sensory Evaluation 12

The gummy candy obtained in each of the above-mentioned Examples, Comparative Example, and Reference Example was held in the mouth, and four expert panelists performed a sensory test for "bitterness" sensed during a period in which the gummy candy was chewed up while being mixed well with saliva. The sensory test was performed when the four expert panelists had agreed to perform evaluation on the same five-point scale as that of Sensory Evaluation 1, except that the evaluation was performed relative to the gummy candy of Reference Example 14 serving as a standard. Then, the average·BR>L of scores given by the expert panelists was determined. The average of the scores is rounded to the first decimal place.

TABLE 17

|  |  |  | Example 39 | Example 40 | Comparative Example 23 | Reference Example 14 |
|---|---|---|---|---|---|---|
| Analysis value or calculated value (solids) | (A) Non-polymer catechins | mass % | 2.6 | 2.6 | 2.6 | 2.6 |
|  | (B) Rutin | mass % | 0.044 | 0.044 | 0.044 | — |
|  | (C) Astragalin | mass % | 0.031 | 0.0052 | — | — |
|  | Mass ratio [(B)/(A)] [×10$^{-2}$][1] | [—] | 1.7 | 1.7 | 1.7 | — |
|  | Mass ratio [(C)/(A)] [×10$^{-3}$][2] | [—] | 12 | 2.0 | — | — |
| Evaluation | Bitterness |  | 4.0 | 3.5 | 1.0 | 3.0 |

[1] Values obtained by multiplying the values in the table by $10^{-2}$
[2] Values obtained by multiplying the values in the table by $10^{-3}$ Example 41

Gum was prepared by a method described below.
1) Commercially available gum (Kracie Holdings, Ltd., Toothbrushing Gum, solids content: 98.0 mass %) was immersed in warm water (300 cc, 50° C.). The dough was kneaded 100 times in the warm water, and then water on its surface was lightly wiped off to prepare a gum dough.
2) A catechin reagent, the rutin reagent, and the astragalin reagent were homogeneously kneaded into the gum dough in the following amounts to obtain gum.

Commercially available gum: 97.3 parts by mass,
Catechin reagent I: 2.0 parts by mass,
Rutin reagent: 0.034 part by mass,
Astragalin reagent: 0.024 part by mass The obtained gum was analyzed, and the sensory evaluation was conducted by a method described below. The results are shown in Table 18.

Example 42

Gum was obtained by the same operations as those of Example 41, except that the blending amount of the astragalin reagent was changed. The obtained gum was subjected to analysis and sensory evaluation in the same manner as in Example 41. The results are shown in Table 18.

Comparative Example 24

Gum was obtained by the same operations as those of Example 41, except that the astragalin reagent was not blended. The obtained gum was subjected to analysis and sensory evaluation in the same manner as in Example 41. The results are shown in Table 18.

Reference Example 15

Gum was obtained by the same operations as those of Example 41, except that the rutin reagent and the astragalin reagent were not blended. The obtained gum was subjected to analysis and sensory evaluation in the same manner as in Example 41. The results are shown in Table 18.

Sensory Evaluation 13

The gum obtained in each of the above-mentioned Examples, Comparative Example, and Reference Example was held in the mouth, and four expert panelists performed a sensory test for "bitterness" sensed during a period in which the gum was chewed 60 times in such a manner that upper and lower back teeth occluded well each time. The sensory test was performed when the four expert panelists had agreed to perform evaluation on the same five-point scale as that of Sensory Evaluation 1, except that the evaluation was performed relative to the gum of Reference Example 15 serving as a standard. Then, the average of scores given by the expert panelists was determined. The average of the scores is rounded to the first decimal place.

TABLE 18

|  |  |  | Example 41 | Example 42 | Comparative Example 24 | Reference Example 15 |
|---|---|---|---|---|---|---|
| Analysis value or calculated value (solids) | (A) Non-polymer catechins | mass % | 2.0 | 2.0 | 2.0 | 2.0 |
|  | (B) Rutin | mass % | 0.034 | 0.034 | 0.034 | — |
|  | (C) Astragalin | mass % | 0.024 | 0.0050 | — | — |
|  | Mass ratio [(B)/(A)] [×10$^{-2}$][1] | [—] | 1.7 | 1.7 | 1.7 | — |

TABLE 18-continued

|  |  |  | Example 41 | Example 42 | Comparative Example 24 | Reference Example 15 |
|---|---|---|---|---|---|---|
|  | Mass ratio [(C)/(A)] [×10$^{-3}$]$^{2)}$ | [—] | 12 | 2.5 | — | — |
| Evaluation | Bitterness |  | 4.0 | 3.8 | 1.0 | 3.0 |

[1)] Values obtained by multiplying the values in the table by 10$^{-2}$
[2)] Values obtained by multiplying the values in the table by 10$^{-3}$ Example 43

90 Parts by mass of green juice powder (Yamamoto Kanpoh Pharmaceutical Co., Ltd., Oomugi Wakaba Powder 100%, non-polymer catechins: 0.54 mass %, rutin: N.D., astragalin: N.D., solids content: 87.7 mass %), 8.3 parts by mass of the catechin reagent I, 0.18 part by mass of the rutin reagent, and 0.010 part by mass of the astragalin reagent were added together, and lastly, the excipient was blend so as to adjust a total amount to 100 parts by mass, followed by homogeneous mixing, to obtain 3 g of green juice powder of the mixture. The obtained green juice powder was analyzed, and the sensory evaluation was conducted by a method described below. The results are shown in Table 19. The contents of the obtained green juice powder had solids content of 90.9 mass %.

Example 44

Green juice powder was obtained by the same operations as those of Example 43, except that the blending amount of the astragalin reagent was changed. The obtained green juice powder was subjected to analysis and sensory evaluation in the same manner as in Example 43. The results are shown in Table 19. The contents of the obtained green juice powder had solids content of 90.9 mass %.

Comparative Example 25

Green juice powder was obtained by the same operations as those of Example 43, except that the astragalin reagent was not blended. The obtained green juice powder was subjected to analysis and sensory evaluation in the same manner as in Example 43. The results are shown in Table 19. The contents of the obtained green juice powder had solids content of 90.9 mass %.

Reference Example 16

Green juice powder was obtained by the same operations as those of Example 43, except that the rutin reagent and the astragalin reagent were not blended. The obtained green juice powder was subjected to analysis and sensory evaluation in the same manner as in Example 43. The results are shown in Table 19. The contents of the obtained green juice powder had solids content of 90.9 mass %.

Sensory Evaluation 14

3 g of the green juice powder obtained in each of the above-mentioned Examples, Comparative Example, and Reference Example was diluted with 100 mL of water at 20° C. to prepare each beverage, and four expert panelists performed a sensory test for "bitterness" at a time when each beverage was drunk. The sensory test was performed when the four expert panelists had agreed to perform evaluation on the same five-point scale as that of Sensory Evaluation 1, except that the evaluation was performed relative to the beverage of Reference Example 16 serving as a standard. Then, the average of scores given by the expert panelists was determined. The average of the scores is rounded to the first decimal place.

TABLE 19

|  |  |  |  | Example 43 | Example 44 | Comparative Example 25 | Reference Example 16 |
|---|---|---|---|---|---|---|---|
| Analysis value or calculated value (solids) | (A) Non-polymer catechins | mass % |  | 9.5 | 9.5 | 9.5 | 9.5 |
|  | (B) Rutin | mass % |  | 0.19 | 0.19 | 0.19 | — |
|  | (C) Astragalin | mass % |  | 0.019 | 0.11 | — | — |
|  | Mass ratio [(B)/(A)] [×10$^{-2}$]$^{1)}$ | [—] |  | 2.1 | 2.1 | 2.1 | — |
|  | Mass ratio [(C)/(A)] [×10$^{-3}$]$^{2)}$ | [—] |  | 2.0 | 12 | — | — |
| Evaluation | Bitterness |  |  | 3.5 | 4.0 | 1.0 | 3.0 |

[1)] Values obtained by multiplying the values in the table by 10$^{-2}$
[2)] Values obtained by multiplying the values in the table by 10$^{-3}$

Example 45

1 g of the oral composition obtained in Example 3 was sprinkled on 30 g of yogurt (Meiji Co., Ltd., Meiji Bulgaria Yogurt LB81 Plain) to obtain a dairy food. The obtained dairy food was subjected to sensory evaluation by a method described below. The result is shown in Table 20.

Comparative Example 26

A dairy food was obtained by the same operation as that of Example 45, except that 1 g of the oral composition obtained in Comparative Example 1 was used. The obtained dairy food was subjected to sensory evaluation in the same manner as in Example 45. The result is shown in Table 20.

Reference Example 17

A dairy food was obtained by the same operation as that of Example 45, except that 1 g of the oral composition obtained in Reference Example 1 was used. The obtained dairy food was subjected to sensory evaluation in the same manner as in Example 45. The result is shown in Table 20.

Sensory Evaluation 15

3 g of the dairy food obtained in each of the above-mentioned Example, Comparative Example, and Reference Example was scooped up with a teaspoon and then held in the mouth, and "bitterness" at a time when the dairy food completely disappeared by being mixed with saliva through use of the tongue was evaluated by four expert panelists, who had agreed to perform evaluation on the same five-point scale as that of Sensory Evaluation 1, except that the evaluation was performed relative to the dairy product of Reference Example 17 serving as a standard. Then, the average of scores given by the expert panelists was determined. The average of the scores is rounded to the first decimal place.

TABLE 20

| | | Example 45 | Comparative Example 26 | Reference Example 17 |
|---|---|---|---|---|
| Evaluation | Bitterness | 4.5 | 1.0 | 3.0 |

Example 46

A seasoning for rice soup was obtained by mixing 1 g of the oral composition obtained in Example 3 with 6 g of a seasoning for rice soup (Ochazuke Nori, Nagatanien Co., Ltd.). The obtained seasoning for rice soup was subjected to sensory evaluation by a method described below. The result is shown in Table 21.

Comparative Example 27

A seasoning for rice soup was obtained by the same operation as that of Example 31, except that 1 g of the oral composition obtained in Comparative Example 1 was used. The obtained seasoning for rice soup was subjected to sensory evaluation in the same manner as in Example 46. The result is shown in Table 21.

Reference Example 18

A seasoning for rice soup was obtained by the same operation as that of Example 31, except that 1 g of the oral composition obtained in Reference Example 1 was used. The obtained seasoning for rice soup was subjected to sensory evaluation in the same manner as in Example 46. The result is shown in Table 21.

Sensory Evaluation 16

6 g of the seasoning for rice soup obtained in each of the above-mentioned Example, Comparative Example, and Reference Example was uniformly sprinkled on 100 g of white rice, and then 150 mL of warm water at 60° C. was poured thereon. Four expert panelists performed a sensory test for "bitterness" at a time when the resultant food was eaten. The sensory test was performed when the four expert panelists had agreed to perform evaluation on the same five-point scale as that of Sensory Evaluation 1, except that the evaluation was performed relative to the seasoning for rice soup of Reference Example 18 serving as a standard. Then, the average of scores given by the expert panelists was determined. The average of the scores is rounded to the first decimal place.

TABLE 21

| | | Example 46 | Comparative Example 27 | Reference Example 18 |
|---|---|---|---|---|
| Evaluation | Bitterness | 4.5 | 1.0 | 3.0 |

As apparent from Tables 1 to 19, when the oral composition containing non-polymer catechins and rutin at a specific quantitative ratio was caused to contain astragalin at a predetermined quantitative ratio with respect to the non-polymer catechins, the oral composition achieved a reduction in bitterness of the non-polymer catechins, even though being rich in non-polymer catechins and rutin. In addition, as apparent from Tables 20 and 21, the oral composition of the present invention, even when added to a food and beverage, did not impair the original taste and flavor of the food and beverage, and hence can also be used as a food additive.

The invention claimed is:

1. An oral composition, comprising the following components (A), (B), (C), and (D):
    (A) non-polymer catechins;
    (B) rutin;
    (C) astragalin; and
    (D) vanillin,
    wherein a content of the component (A) in solids is from 2 mass % to 50 mass %,
    wherein a content of the component (D) in solids is from $0.05 \times 10^{-4}$ mass % to $100 \times 10^{-4}$ mass %,
    wherein a mass ratio of the component (B) to the component (A), [(B)/(A)], is from $0.05 \times 10^{-2}$ to $50 \times 10^{-2}$, and
    wherein a mass ratio of the component (C) to the component (A), [(C)/(A)], is from $7.0 \times 10^{-3}$ to $50 \times 10^{-3}$.

2. The oral composition according to claim 1, wherein the mass ratio of the component (B) to the component (A), [(B)/(A)], is from $0.06 \times 10^{-2}$ to $40 \times 10^{-2}$.

3. The oral composition according to claim 1, wherein the mass ratio of the component (C) to the component (A), [(C)/(A)], is from $7.0 \times 10^{-3}$ to $40 \times 10^{-3}$.

4. The oral composition according to claim 1, wherein a content of the component (B) in the solids is from 0.005 mass % to 1.0 mass %.

5. The oral composition according to claim 1, wherein a content of the component (C) in the solids is from 0.005 mass % to 1.0 mass %.

6. The oral composition according to claim 1, wherein a ratio of gallate forms in the component (A) is from 35 mass % to 63 mass %.

7. The oral composition according to claim 1, wherein the mass ratio of the component (B) to the component (A), [(B)/(A)], is from $0.08 \times 10^{-2}$ to $20 \times 10^{-2}$.

8. The oral composition according to claim 1, wherein the mass ratio of the component (C) to the component (A), [(C)/(A)], is from $7.0 \times 10^{-3}$ to $30 \times 10^{-3}$.

9. The oral composition according to claim 1, further comprising an excipient.

10. The oral composition according to claim 1, which is an oral composition in a solid form.

11. The oral composition according to claim 1, which is in a form of a granule or a tablet.

12. The oral composition according to claim 1, which is an instant beverage.

13. The oral composition according to claim 1, wherein the oral composition is chocolate.

14. A food and beverage, comprising the oral composition according to claim 1.

15. The food and beverage according to claim 14, wherein the oral composition is present in an amount of from 0.01 parts by mass to 30 parts by mass in terms of solids, with respect to 100 parts by mass of the food and beverage.

* * * * *